(12) United States Patent
Frost et al.

(10) Patent No.: US 9,956,221 B2
(45) Date of Patent: *May 1, 2018

(54) USE OF A RECEPTOR-TYPE KINASE MODULATOR FOR TREATING POLYCYSTIC KIDNEY DISEASE

(71) Applicant: Symphony Evolution, Inc., Rockville, MD (US)

(72) Inventors: Philip Frost, Rockville, MD (US); William W. N. Liao, Rockville, MD (US); Eric K. Rowinsky, Rockville, MD (US)

(73) Assignee: SYMPHONY EVOLUTION, INC., Rockville, MD (US)

(*) Notice: Subject to any disclaimer, the term of this patent is extended or adjusted under 35 U.S.C. 154(b) by 0 days. days.

This patent is subject to a terminal disclaimer.

(21) Appl. No.: 15/158,171

(22) Filed: May 18, 2016

(65) Prior Publication Data

US 2016/0367555 A1 Dec. 22, 2016

Related U.S. Application Data

(63) Continuation of application No. 13/818,844, filed as application No. PCT/US2011/049077 on Aug. 25, 2011, now Pat. No. 9,364,479.

(60) Provisional application No. 61/377,211, filed on Aug. 26, 2010.

(51) Int. Cl.
*A61K 31/517* (2006.01)
*A61K 9/08* (2006.01)
*A61K 9/20* (2006.01)

(52) U.S. Cl.
CPC .............. *A61K 31/517* (2013.01); *A61K 9/08* (2013.01); *A61K 9/20* (2013.01); *A61K 9/2009* (2013.01); *A61K 9/2013* (2013.01); *A61K 9/2018* (2013.01); *A61K 9/2027* (2013.01); *A61K 9/2054* (2013.01)

(58) Field of Classification Search
CPC .. A61K 31/517; A61K 9/2027; A61K 9/2018; A61K 9/2013; A61K 9/2009; A61K 9/20; A61K 9/08; A61K 9/2054
See application file for complete search history.

(56) References Cited

U.S. PATENT DOCUMENTS 7,576,074 B2  8/2009  Rice et al.

FOREIGN PATENT DOCUMENTS

| WO | 03/050090 | 6/2003 |
|----|-----------|--------|
| WO | 2004/006846 | 1/2004 |
| WO | 06/042100 | 4/2006 |
| WO | 08/070117 | 6/2008 |
| WO | 08/122779 | 10/2008 |

OTHER PUBLICATIONS

McConathy et al (Primary Care Companion J Clin Psychiatry 2003;5:70-73).*
McConathy et al ((Primary Care Companion J Clin Psychiatry 2003;5(2)) (Year: 2003).*
Tao et al., "VEGF receptor inhibition slows the progression of polycystic kidney disease", Kidney International, 2007, 72(11), 1358-1366.
Sweeney et al., "Src inhibition ameliorates polycystic kidney disease", Journal of the American Society of Nephrology, 2008, 19(7), 1331-1341.
McNeil, C., "Two targets, one drug for new EGFR inhibitors", Journal of the National Cancer Institute, 2006, 98(16), 1102-1103.
Minguez et al., "Molecular therapy of hepatocellular carcinoma with sorafenib combined with abrogation of EGFR signaling with XL647 (EGFR/HER2/NU/VEGFR inhibitor, compared to eriotinib in vivo", Hepatology, 2009, 50(4), Suppl. S, p. 856A.
Wilson et al., Biochimica et Biophysica Acta 1762 (2006) 647-655.
Lyons et al., J Am Soc nephrol 15:2548-2555, 2004.
Looper et al., Veterinary and Comparative Oncology, 4, 1, 33-40.
Naiyer et al., Journal of Thoracic Oncology:vol. 2(8) Supplement Aug. 4, 2007 p. S737.
MedKoo Biosciences, http://www.medkoo.com/Anticancer-trials/XL647.htm, accessed Sep. 4, 2014.

* cited by examiner

*Primary Examiner* — Angela C Brown-Pettigrew
(74) *Attorney, Agent, or Firm* — McDonnell Boehnen Hulbert & Berghoff LLP

(57) ABSTRACT

The invention comprises a method of treating polycystic kidney disease (PKD) in a mammal, such as a human or feline (e.g., Persian cat), comprising administering a therapeutically effective amount of the compound of formula

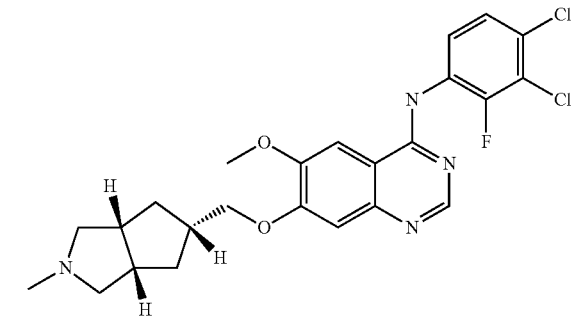

to the mammal. Also provided are uses of the compound for preparation of a medicament for treating PKD and the above compound and compositions comprising it for treating PKD.

27 Claims, No Drawings

USE OF A RECEPTOR-TYPE KINASE MODULATOR FOR TREATING POLYCYSTIC KIDNEY DISEASE

CROSS-REFERENCE TO RELATED APPLICATIONS

This application is a continuation of U.S. patent application Ser. No. 13/818,844, filed May 7, 2013, which is a U.S. national stage of International Application PCT/US2011/049077, filed Aug. 25, 2011, which claims priority to U.S. Provisional Application 61/377,211, filed Aug. 26, 2010, the specification, abstract, and claims of each of which is hereby incorporated into the present specification by reference.

BACKGROUND OF THE INVENTION

Field of the Invention

This invention relates to compounds for modulating multiple protein kinase enzymatic activities for affecting cellular activities such as proliferation, differentiation and programmed cell death. Specifically, the invention relates to quinazolines that inhibit, regulate and/or modulate a set of kinase enzymes and receptor signal transduction pathways related to the changes in cellular activities as mentioned above, compositions which contain these compounds, and methods of using them to treat kinase-dependent diseases and conditions. Even more specifically, the invention relates to the use of a kinase inhibitor compound that downregulates a unique group of kinases active in the progression of polycystic kidney disease (PKD) and to methods of treating PKD.

Summary of Related Art

The development of targeted therapy focused initially on the search for drugs that could specifically target a selected kinase enzyme essential for cell proliferation in cancer. The purpose of searching for selectivity was to try and limit toxicity. This approach was generally unsuccessful because it was difficult to achieve single kinase target inhibition due to the "overlap" and homology of the active kinase domains of the known 540 kinases. Secondly, it has become increasingly clear that focused targeting results in the selection for cells capable of circumventing any single point of inhibition in a pathway. Current thinking leans towards targeting multiple sites in single or multiple pathways. This observation, learned from experience in oncology can be applied to other diseases (as outlined below).

Protein kinases are enzymes that catalyze the phosphorylation of proteins, in particular, hydroxy groups on tyrosine, serine and threonine residues of proteins. The consequences of this seemingly simple activity are staggering, influencing cell differentiation and proliferation. Virtually all aspects of cell life in one-way or another depend on protein kinase activity. Furthermore, abnormal protein kinase activity has been related to a host of disorders, ranging from relatively non-life threatening diseases such as psoriasis to extremely virulent diseases such as glioblastoma (brain cancer).

Protein kinases can be categorized as receptor type or non-receptor type. Receptor-type tyrosine kinases have an extracellular, a transmembrane, and an intracellular domain, while non-receptor type tyrosine kinases are wholly intracellular.

Receptor-type tyrosine kinases are comprised of a large number of transmembrane receptors with diverse biological activity. In fact, about twenty different subfamilies of receptor-type tyrosine kinases have been identified. One tyrosine kinase subfamily, designated the HER subfamily, is comprised of EGFR (HER1), HER2, HER3, and HER4. Ligands of this subfamily of receptors identified so far include epithelial growth factor, TGF-alpha, amphiregulin, HB-EGF, betacellulin and heregulin. Another subfamily of these receptor-type tyrosine kinases is the insulin subfamily, which includes INS-R, IGF-IR, and IR-R. The PDGF subfamily includes the PDGF-alpha and beta-receptors, CSFIR, c-kit and FLK-II. Additionally there is the FLK family, which is comprised of the kinase insert domain receptor (KDR), fetal liver kinase-1 (FLK-1), fetal liver kinase-4 (FLK-4) and the fms-like tyrosine kinase-1 (fit-1). The PDGF and FLK families are usually considered together due to the similarities of the two groups. For a detailed discussion of the receptor-type tyrosine kinases, see Plowman et al., 1994 *DN&P* 7(6):334-339, which is hereby incorporated by reference for all purposes.

The non-receptor type of tyrosine kinases is also comprised of numerous subfamilies, including Src, Frk, Btk, Csk, Abl, Zap70, Fes/Fps, Fak, Jak, Ack, and LIMK. Each of these subfamilies is further sub-divided into varying receptors. For example, the Src subfamily is one of the largest and includes Src, Yes, Fyn, Lyn, Lck, Blk, Hck, Fgr, and Yrk. The Src subfamily of enzymes has been linked to oncogenesis. For a more detailed discussion of the non-receptor type of tyrosine kinases, see Bolen, *Oncogene,* 8:2025-2031 (1993), which is hereby incorporated by reference for all purposes.

Deregulation of protein kinase enzymatic activity can lead to altered cellular properties, such as uncontrolled cell growth associated with cancer. In addition to oncological indications, altered kinase signaling is implicated in numerous other pathological diseases. These include, but are not limited to: immunological disorders, cardiovascular diseases, inflammatory diseases, and degenerative diseases. Therefore, both receptor and non-receptor protein kinases are attractive targets for small molecule drug discovery.

One particularly attractive goal for therapeutic use of kinase modulation relates to oncological indications. For example, modulation of protein kinase activity for the treatment of cancer has been demonstrated successfully with the FDA approval of Gleevec® (imatinib mesylate, produced by Novartis Pharmaceutical Corporation of East Hanover, N.J.) for the treatment of Chronic Myeloid Leukemia (CML) and gastrointestinal stroma cancers (GIST). Gleevec is a c-Kit and Abl kinase inhibitor.

Modulation (particularly inhibition) of cell proliferation and angiogenesis, two key cellular processes needed for tumor growth and survival (Matter A. 2001 *Drug Disc Technol* 6:1005-1024), is an attractive goal for development of small-molecule drugs. Anti-angiogenic therapy represents a potentially important approach for the treatment of solid tumors and other diseases associated with dysregulated vascularization, including ischemic coronary artery disease, diabetic retinopathy, psoriasis and rheumatoid arthritis. Also, cell antiproliferative agents are desirable to slow or stop the growth of tumors.

Inhibition of EGF, VEGF and ephrin signal transduction will prevent cell proliferation and angiogenesis, two key cellular processes needed for tumor growth and survival (Matter A. 2001 *Drug Disc Technol* 6:1005-1024). VEGF receptors are previously described targets for small molecule inhibition.

The Eph receptors comprise the largest family of receptor tyrosine kinases and are divided into two groups, EphA and EphB, based on their sequence homology. The ligands for the Eph receptors are ephrins, which are membrane anchored. Ephrin A ligands bind preferentially to EphA receptors whilst ephrin B ligands bind to EphB receptors. Binding of ephrin to Eph receptors causes receptor autophosphorylation and typically requires a cell-cell interaction because both receptor and ligand are membrane bound.

Overexpression of Eph receptors has been linked to increased cellular proliferation in a variety of tumors (Zhou R 1998 *Pharmacol Ther.* 77:151-181; Kiyokawa E, Takai S, Tanaka M et al 1994 *Cancer Res* 54:3645-3650; Takai N Miyazaki T, Fujisawa K, Nasu K and Miyakawa. 2001 *Oncology Reports* 8:567-573). The family of Eph receptor tyrosine kinases and their ephrin ligands play important roles in a variety of processes during embryonic development and also in pathological angiogenesis and potentially metastasis. Therefore modulation of Eph receptor kinase activity should provide means to treat or prevent disease states associated with abnormal cell proliferation such as those described above.

The epidermal growth factor receptor (EGFR, HER1, erbB1) is part of a family of plasma membrane receptor tyrosine kinases that control cellular growth, proliferation, and apoptosis. The ligand for EGFR is the epidermal growth factor and dysregulation of the EGFR signal transduction pathway has been implicated in tumorigenesis and cancer progression, thus making it a clinically relevant target for novel anticancer treatments (Drevs J et at 2003 *Curr Drug Targets* 4, 113-121; Ciardiello F and Tortora G. 2001 *Clin. Cancer Res.* 7:2958-2970; Thomas M. 2002 *Semin Onc. Nurs.* 18:20-27).

EGFR is overexpressed in different human cancers, especially non-small cell lung cancer and glioblastomas. In these cancers, EGFR overexpression is commonly associated with advanced disease and poor prognosis (Baselga J et at 1999 *Semin. Oncol.* 26:78-83).

"Polycystic kidney disease" (PKD) refers to a group of monogenic disorders that result in the development of bilateral renal cysts ultimately leading to kidney failure. PKD is the most common of all life-threatening genetic diseases, and affects 12-15 million people worldwide. There are two major forms of PKD: autosomal recessive (ARPKD) and autosomal dominant (ADPKD). ARPKD is a less-frequently inherited form of the disease that often causes significant mortality in the first months of life. ARPKD is caused by a mutation in the PKHD1 gene, while ADPKD is caused by a mutation in either the PKD1 or PKD2 gene (and thus these forms are referred to as type 1 or type 2 ADPKD). These single mutations result in dramatic changes in the ability of renal tubular cells to maintain their planar polarity (position within the organ), and to control their proliferation. ADPKD is the most common inherited genetic disease. Because each individual has one normal allele inherited from their non-carrier parent, the dominant mutant gene does not manifest its effects until the normal allele is lost or inactivated. Thus, some patients develop symptoms in childhood while most become symptomatic by age 40 depending on when the normal allele is lost. The biochemical mechanism responsible for the clinical findings associated with PKD is thought to relate to abnormalities in calcium ion channels.

As noted above, PKD is characterized by the bilateral formation and growth of multiple cysts that lead to the alteration of the kidney architecture, deformed nephrons and renal failure. In ADPKD, cysts form when the proliferation of renal tubular cells leads to obstruction of normal tubular flow. The renal tubular cells that form the inner lining of the cysts retain their normal secretary functions and fill the cysts with fluid that contains many receptor ligands (signaling proteins) such as TGF-alpha and EGF (Wilson S J et at 2006 *Biochim Biophys Acta* July; 1762(7):647-55). As the cysts enlarge, the kidneys enlarge to as much as 20-30 pounds in late stage disease.

Human clinical symptom in ADPKD patients include abdominal and flank pain (as the cysts enlarge), hypertension, liver cysts, hematuria, infection and ultimately renal failure. No specific treatment for the prevention of the progression of PKD is available (Grantham J J 2008 *NEJM* 359:1477-1485).

Similarly, PKD affects approximately 38% of Persian cats worldwide, making it the most prominent inherited feline disease (Young A E et at 2005 *Mammalian Genome* 16:59-65). It mimics human disease and is secondary to a mutation in the PKD1 gene.

SUMMARY OF THE INVENTION

Many strategies have been proposed for treating PKD, but few have been applied. We propose herein a treatment modality based on inhibiting at least four (4) kinases—three receptor tyrosine kinases (HER1, HER2, and VEGFR) and one cytoplasmic tyrosine kinase (SRC). Our proposal emphasizes the need to target all four kinases to achieve effective inhibition of the progression of PKD.

Thus, in one aspect, the invention is directed to methods of treating PKD with the compounds and compositions disclosed herein.

In another aspect, the invention comprises the use of a compound or composition disclosed herein for the manufacture of a medicament for the treatment of PKD.

In another aspect, the invention comprises compounds and compositions for use in treating PKD.

These and other features and advantages of the present invention will be described in more detail below.

DETAILED DESCRIPTION OF THE INVENTION

We recognized that XL-647 (also known as PRIM-001 and KD019) and related compounds (which are described in U.S. Pat. No. 7,576,074, hereby incorporated by reference in its entirety) are unique in targeting the key elements of the EGFR signaling cascade as well as VEGF-R, which, as described below, are implicated in PKD. Thus, we recognized that such compounds provide all the necessary inhibition for treatment of PKD in a single compound. The potency of XL-647 activity against each target is such as to predict a lower dose than used in oncology clinical studies. XL-647 is less toxic than each of the single targeting agents alone and would clearly be less toxic than those agents used in combination. The use of XL-647 in PKD would therefore provide broad spectrum activity against the key targets and add the benefit of reduced VEGF-R activity and potentially improved safety profile in the kidney.

Earlier descriptions of the role of Epidermal Growth Factor Receptor (EGFR) in PKD were presented by Du and Wilson (Grantham J J 2008 *NEJM* 359:1477-1485; Wilson P D et at 1993 *Eur J Cell Biol* June; 61(1):131-8; Du J and Wilson P D 1995 *Am J Physiol Cell Physiol* 269: C487-C495) and extended by Sweeney and Avner (Sweeney W E and Avner E D 1998 *Am J Physiol* 275:387-394). Cell lines were derived by inter-crossing breeding of bpk mice (a murine model of ARPKD) and the Immorto mouse (Sweeney W E et at 2001 *Am J Physiol Cell Physiol* 281:1695-1705). These animals developed enlarged cystic kidneys as well as biliary ducal ectasia resulting in renal failure and hepatic abnormalities. Cystic cell lines were established in vitro and demonstrated a mis-localization of the EGFR to their apical surface. This was confirmed in vivo and substantiated by Wilson and Du (Wilson P D et at 1993 *Eur J Cell Biol* June; 61(1):131-8; Du J and Wilson P D 1995 *Am J Physiol Cell Physiol* 269: C487-C495), who had also demonstrated a role TGF-alpha and EGF in renal tubular cell proliferation in PKD. Furthermore, human cyst fluid was shown to contain EGF and TGF-alpha (Wilson S J et at 2006 *Biochim Biophys Acta* July; 1762(7):647-55; Klinger R et at 1992 *Am J Kidney Dis* 19(1):22-30). This mis-localization of EGFR was validated in both additional murine models and human tissues in ARPKD and ADPKD (Wilson P D et at 1993 *Eur J Cell Biol* June; 61(1):131-8; Du J and Wilson P D 1995 *Am J Physiol Cell Physiol* 269: C487-C495; Avner E D and Sweeney W E 1995 *Pediatr Res* 37:359A; Orellana S A et at 1995 *Kidney Int* 47:490-499; Richards W G et at 1998 *J Clin Invest* 101:935-939). Pugh et al (Pugh J L et al 1995 *Kidney Int* 47:774-781) further showed elevated EGFR tyrosine kinase activities in PKD. Finally, crossing the hypomorphic EGFR allele (waved-2) into cystic mice carrying the orpk (Oak Ridge Polycystic Kidney) mouse mutation, significantly reduced EGFR activity and cyst formation (Richards W G et at 1998 *J Clin Invest* 101:935-939). Subsequent studies have shown a potential role for EGFR ligands in promoting cytogenic disease. Both EGF and TGF-alpha are cystogenic in vitro (Pugh J L et al 1995 *Kidney Int* 47:774-781; Avner E D and Sweeney W E 1990 *Pediatr Nephrol* 4:372-377; Neufield T K et at 1992 *Kidney Int* 41:1222-1236). Cystic kidneys have increased EGF-alpha RNA expression and renal cyst fluid from PKD murine and rat models contained multiple EGF peptides at mitogenic concentrations (Lowden D A et at 1994 *J Lab Clin Med* 124, 386-394).

While the exact mechanism by which mutant PKD genes results in EGFR abnormalities are not well characterized, it was logical to assess the effect of EGFR inhibition on cyst development in rodent models of PKD. Sweeney et. al. (Sweeney W E et at 2000 *Kidney Int* 57:33-40) showed that the treatment of bpk mice with the EGFR kinase inhibitor (EKI-785) was effective in preventing the progression of PKD. Animals maintained on EKI-785 survived for long periods but progressed when the drug was removed (Sweeney et at 2000 *Kidney Int* 57:33-40). This finding was confirmed using two different EGFR inhibitors.

Evidence for the role of EGFR in PKD was further supported by the demonstration that inhibition EGFR ligand release can also ameliorate PKD. The treatment of bpk mice with a TACE (TNF-alpha converting enzyme) inhibitor resulted in a dramatic reduction in kidney size and increased animal survival (Dell K M et at 2001 *Kidney Int* 60:1240-1248). TACE is a member of the metalloproteinase enzyme family whose function is to process prepropeptides to allow for the shredding of the active peptide. In PKD, inhibition of the TACE enzyme ADAM-17 reduces the release of TGF-alpha resulting in decrease in EGFR activation.

Subsequent analyses by Wilson et. al. (Wilson S J et at 2006 *Biochim Biophys Acta* July; 1762(7):647-55) have further shown a role for HER-2 as part of the mis-localization of the EGFR complex. In some animal models, HER-2 appears to be the dominant EGFR inducing cell tubular cell proliferation. The PCK rat is such a model where specific HER-2 inhibitors (two have been tested) are effective in preventing the development of PKD. Some argue that heterodimers and HER-1 and HER-2 are a major factor in disease progression (Wilson S J et at 2006 *Biochim Biophys Acta* July; 1762(7):647-55). Thus, a bi-functional HER-1/HER-2 kinase inhibitor would be more likely to be effective in treatment.

EGFR activation results in a cascade of events that ultimately affects DNA transcription factors and protein production. One of the key elements in the signaling events from EGFR is mediated by the cytoplasmic enzyme SRC. If the inhibition the EGFR kinase domain inhibits disease progression, it is logical that the same result could occur by inhibiting a member of the signaling pathway, e.g., SRC. SRC was chosen as a target because it acts by affecting multiple steps in at least two signaling pathways (MER/ERK and PKA/bRAF). In addition, SRC is known to facilitate EGFR activity and to enhance EGFR phosphorylation of downstream targets (Browman P A et at 2004 *Oncogene* 23:7957-68; Roskoski R 2005 *Biochem Biophys Res Commun* 331:1-14). SRC also stimulates the activation of MMPs at the cell membrane and enhances ligand release. The treatment of bpk mice or PCK rat with the SRC inhibitor SKI-606 ameliorated renal cyst formation and biliary duct abnormalities in both the HER-1 and HER-2 dependent rodent model (Roskoski R 2005 *Biochem Biophys Res Commun* 331:1-14). SRC inhibition is also correlated with a reduction in elevated cAMP (Roskoski R 2005 *Biochem Biophys Res Commun* 331:1-14).

VEGF plays a major role in angiogenesis during wound healing and tumor formation. VEGF ligand is produced in response to hypoxia and the production of HIF1-alpha. VEGF is present in PKD cyst fluid and is thought to be a response to hypoxia produced by the mechanical destruction and vascular restriction caused by the cysts. VEGR-1 and VEGR-2 are present in renal endothelial cells and is hypothesized that activation of the VEGF pathway facilitates cyst growth by fostering neo-vascularization in a manner similar that those proposed for tumors. Therefore, inhibition of VEGFR would prevent vessel growth and reduce renal cyst enlargement.

Individual kinase inhibitors active against HER-1, HER-2 or SRC (Wilson S J et at 2006 *Biochim Biophys Acta* July; 1762(7):647-55; Lowden D A et al 1994 *J. Lab. Clin. Med.* 124, 386-394; Swenney W E et at 2008 *J Am Soc Nephrol* 19: 1331-1341) have shown to be active in rodent models of PKD. The present invention is based on the position that a combination of agents would be more clinically effective and at lower doses. Use of combination therapy has a precedent in oncology where single agents are almost never used. In fact, this principal has been proven by experiments in a PKD model where we treated animals with a combination of EGFR (EKB-569) and TACE inhibitors. While the EGFR inhibitor was effective in reducing cyst formation and maintaining normal renal function; the addition of a TACE inhibitor allowed for a reduction of EKB-569 dose by 67%, while achieving and equivalent effect of EKB-569 alone at a higher dose (Sweeney W E et at 2003 *Kidney Int* 64:1310-1319).

While in theory a combination therapy could be used by simply amalgamating drugs that individually target HER-1, HER-2, SRC and VEGF-R, this is unlikely to occur as a practical matter due to the regulatory complexity and commercial constraints. In addition, the spectrum of kinase activity would be exceedingly broad resulting in an increased risk of toxicity. For example, a combination of Lapatanib with Sunitinib would not only affect ERB-1, ERB-2 and VEGF-R but also target ERK-1, ERK-2, AKT, Cyclin-D, PDGFR, cKIT and FLT-3, while not affecting SRC. If one would add Dastinib to this combination, one would affect SRC but also ABL and potentially increase toxicity by excessive inhibition of cKIT and PDGFR. Furthermore, clinical trials of these combination studies would be overly complex and likely not achievable in any reasonable period of time. For example, each drug has different PK/PD characteristics and there may be overlapping toxicities thus complicating dosing schedules. Finally, the cost of combining three or four agents from different manufacturers may be prohibitive.

We have discovered that XL-647 and related compounds can target HER-1, HER-2, SRC and VEGF-R and, therefore, obviate the need for and overcome the complications associated with combination therapies.

Thus, in one aspect, the invention is directed to methods of treating PKD with XL-647 or a related compound and pharmaceutically acceptable compositions thereof. Such pharmaceutically acceptable compositions comprise XL-647 or a related compound and a pharmaceutically acceptable carrier, diluent, and/or excipient. In some embodiments the carrier is water. In other embodiments the carrier is other than water.

The methods of the invention comprise administering a therapeutically effective amount of XL-647 or a related compound (or a pharmaceutically acceptable salt thereof) to a mammal having PKD. In one embodiment, XL-647 or a related compound is in the form of a pharmaceutically acceptable composition. In some embodiments the mammal is a human. In others embodiments the mammal is a feline, such as a Persian cat.

In another aspect, the invention comprises the use of a compound or composition disclosed herein for the manufacture of a medicament for the treatment of PKD in a mammal such as a human or a feline, particularly a Persian cat.

In another aspect, the invention comprises compounds and compositions for use in treating PKD in a mammal such as a human or a feline, particularly a Persian cat.

XL-647 is N-(3,4-dichloro-2-fluorophenyl)-7-({[(3aR,5r,6aS)-2-methyloctahydrocyclopenta[c]pyrrol-5-yl]methyl}oxy)-6-(methyloxy)quinazolin-4-amine:

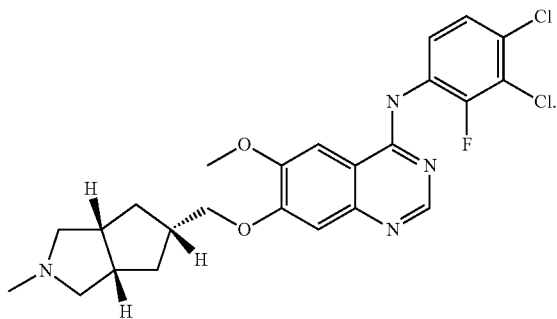 [SMILES: COc1cc2c(Nc3ccc(Cl)c(Cl)c3F)ncnc2cc1OC[C@@H]1C[C@@H]2CN(C)C[C@@H]2C1]

It can be synthesized according to the methods described in U.S. Pat. No. 7,576,074 (see Example 14).

As noted above and used herein, related compounds are those in U.S. Pat. No. 7,576,074 of Formula I

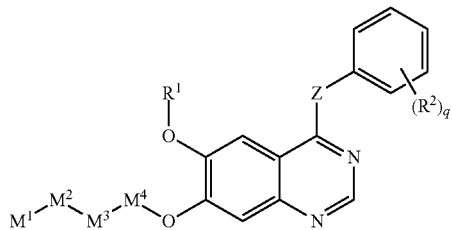

or a pharmaceutically acceptable salt, hydrate, or prodrug thereof, wherein, $R^1$ is $C_1$-$C_3$ alkyl optionally substituted with between one and three $R^{50}$ substituents;

$R^2$ is selected from —H, halogen, trihalomethyl, —CN, —NH$_2$, —NO$_2$, —OR$^3$, —N(R$^3$)R$^4$, —S(O)$_{0-2}$R$^4$, —SO$_2$N(R$^3$)R$^4$, —CO$_2$R$^3$, —C(=O)N(R$^3$)R$^4$, —N(R$^3$)SO$_2$R$^4$, —N(R$^3$)C(=O)R$^3$, —N(R$^3$)CO$_2$R$^4$, —C(=O)R$^3$, optionally substituted lower alkyl, optionally substituted lower alkenyl, and optionally substituted lower alkynyl;

$R^3$ is —H or $R^4$;

$R^4$ is selected from optionally substituted lower alkyl, optionally substituted aryl, optionally substituted lower arylalkyl, optionally substituted heterocyclyl, and optionally substituted lower heterocyclylalkyl; or $R^3$ and $R^4$, when taken together with a common nitrogen to which they are attached, form an optionally substituted five- to seven-membered heterocyclyl, said optionally substituted five- to seven-membered heterocyclyl optionally containing at least one additional heteroatom selected from N, O, S, and P;

q is zero to five;

Z is selected from —OCH$_2$—, —O—, —S(O)$_{0-2}$—, —N(R$^5$)CH$_2$—, and —NR$^5$—;

$R^5$ is —H or optionally substituted lower alkyl;

$M^1$ is —H, $C_1$-$C_8$ alkyl-L$^2$-L$^1$- optionally substituted by $R^{50}$, G(CH$_2$)$_{0-3}$—, or R$^{53}$(R$^{54}$)N(CH$_2$)$_{0-3}$—; wherein G is a saturated five- to seven-membered heterocyclyl containing one or two annular heteroatoms and optionally substituted with between one and three $R^{50}$ substituents; L$^1$ is —C=O— or —SO$_2$—; L$^2$ is a direct bond, —O—, or —NH—; and R$^{53}$ and R$^{54}$ are independently $C_1$-$C_3$ alkyl optionally substituted with between one and three $R^{50}$ substituents;

$M^2$ is a saturated or mono- or poly-unsaturated $C_3$-$C_{14}$ mono- or fused-polycyclic hydrocarbyl optionally containing one, two, or three annular heteroatoms per ring and optionally substituted with between zero and four $R^{50}$ substituents; and $M^3$ is —NR$^9$—, —O—, or absent;

$M^4$ is —CH$_2$—, —CH$_2$CH$_2$—, —CH$_2$CH$_2$CH$_2$—, or absent;

$R^9$ is —H or optionally substituted lower alkyl;

$R^{50}$ is —H, halo, trihalomethyl, —OR$^3$, —N(R$^3$)R$^4$, —S(O)$_{0-2}$R$^4$, —SO$_2$N(R$^3$)R$^4$, —CO$_2$R$^3$, —C(=O)N(R$^3$)R$^4$, —C(=NR$^{25}$)N(R$^3$)R$^4$, —C(=NR$^{25}$)R$^4$, —N(R$^3$)SO$_2$R$^4$, —N(R$^3$)C(O)R$^3$, —NCO$_2$R$^3$, —C(=O)R$^3$, optionally substituted alkoxy, optionally substituted lower alkyl, optionally substituted aryl, optionally substituted lower arylalkyl, optionally substituted heterocyclyl, and optionally substituted lower heterocyclylalkyl; or two of $R^{50}$, when taken together on the same carbon are oxo; or two of $R^{50}$, when taken together with a common carbon to which they are attached, form a optionally substituted three- to seven-membered spirocyclyl, said optionally substituted three- to seven-membered spirocyclyl optionally containing at least one additional heteroatom selected from N, O, S, and P; and $R^{25}$ is selected from —H, —CN, —NO$_2$, —OR$^3$, —S(O)$_{0-2}$R$^4$, —CO$_2$R$^3$, optionally substituted lower alkyl, optionally substituted lower alkenyl, and optionally substituted lower alkynyl, and include the subgenera and species disclosed in U.S. Pat. No. 7,576,074.

XL-647 is an effective therapeutic in a key murine model, the BPK model of ARPKD. The BPK model of ARPKD retains the same altered location of EGFR that is seen in murine and human ADPKD. This model is therefore widely accepted as a general means for affecting the EGFR abnormality in PKD, both ARPKD and ADPKD. The BPK model arose as a spontaneous mutation in an inbred colony of BALB/c mice. Homozygous bpk mice develop massively enlarged kidneys and die of renal failure at an average postnatal age of 24 days (PN-24). The average age of death of untreated affected animals is 25 days with a range of 21-29 days. Extra renal manifestations include biliary proliferation and ductal ectasia. Because of the recessive nature of the disease, wild type+/+ and heterozygous bpk/+ mice are phenotypically normal. The primary measurement used in these studies is a comparison of the kidney weight to body weight ratio (KW/BW). This ratio has consistently been shown to be an accurate assessment of the effectiveness of PKD therapy. Additional measurements include assessment of renal function (BUN, creatinine and MUCA) and histological evaluation of kidney size and collecting tubulescystic index (CT-CI).

In the bpk mice model described below, XL-647 treatment decreased the kidney weight to body weight ratio relative to untreated animals by 21.5% for 7.5 mg/kg q.o.d., 36.7% for 15.0 mg/kg q.o.d., and 41.19% for 15.0 mg/kg q.d. These ratios are comparable or superior to those seen in experiments with single agents ("Src Inhibition ameliorates Polycystic Kidney Disease," *J Am Soc Nephrol* 19: 2008, pp. 1331-1341; "Treatment of PKD with a novel tyrosine kinase inhibitor," *Kidney International*, Vol. 57, 2000, pp. 33-40). XL-647 treatment reduced kidney weight 21.8% with 7.5 mg/kg q.d. and 40.3% with 15 mg/kg q.d. In addition, BUN decreased 42% and 60.5%, creatinine by 8.3% and 25%, while MUCA improved 20.1% and 66.2% (respectively for 7.5 mg/kg q.d. and 15 mg/kg q.d.). The CT-CI index decreased 25% and 45.8% respectively. These findings demonstrate that XL-647 is an effective means for preventing the progression of PKD.

Similarly, XL-647 is an effective therapy in a rodent model, the PCK rat model. Treatment with XL-647 decreased kidney weight by 13.4% with 7.5 mg/kg q.d. and 26.0% with 15 mg/kg q.d. This corresponded with a dose dependent decrease in KW/BW ratio in the treated PCK (diseased) rat. CT-CI was reduced 19.6% and 35.7% respectively for 7.5 mg/kg q.d. and 15 mg/kg q.d. The BUN level decreased by 19.2% with 7.5 mg/kg q.d. and 28.8% with 15 mg/kg q.d.

Administration of XL-647 or a related compound, or their pharmaceutically acceptable salts, in pure form or in an appropriate pharmaceutical composition, can be carried out via any of the accepted modes of administration or agents for serving similar utilities. Thus, administration can be, for example, orally, nasally, parenterally (intravenous, intramuscular, or subcutaneous), topically, transdermally, intravaginally, intravesically, intracisternally, or rectally, in the form of solid, semi-solid, lyophilized powder, or liquid dosage forms, such as for example, tablets, suppositories, pills, soft elastic and hard gelatin capsules, powders, solutions, suspensions, or aerosols, or the like, preferably in unit dosage forms suitable for simple administration of precise dosages.

The compositions will include a conventional pharmaceutical carrier or excipient and a compound of the invention as the/an active agent, and, in addition, may include other medicinal agents, pharmaceutical agents, carriers, adjuvants, etc. Compositions of the invention may be used in combination with anticancer or other agents that are generally administered to a patient being treated for cancer. Adjuvants include preserving, wetting, suspending, sweetening, flavoring, perfuming, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride, and the like. Prolonged absorption of the injectable pharmaceutical form can be brought about by the use of agents delaying absorption, for example, aluminum monostearate and gelatin.

If desired, a pharmaceutical composition of the invention may also contain minor amounts of auxiliary substances such as wetting or emulsifying agents, pH buffering agents, antioxidants, and the like, such as, for example, citric acid, sorbitan monolaurate, triethanolamine oleate, butylalted hydroxytoluene, etc.

Compositions suitable for parenteral injection may comprise physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

One preferable route of administration is oral, using a convenient daily dosage regimen that can be adjusted according to the degree of severity of the disease-state to be treated.

Solid dosage forms for oral administration include capsules, tablets, pills, powders, and granules. In such solid dosage forms, the active compound is admixed with at least one inert customary excipient (or carrier) such as sodium citrate or dicalcium phosphate or (a) fillers or extenders, as for example, starches, lactose, sucrose, glucose, mannitol, and silicic acid, (b) binders, as for example, cellulose derivatives, starch, alignates, gelatin, polyvinylpyrrolidone, sucrose, and gum acacia, (c) humectants, as for example, glycerol, (d) disintegrating agents, as for example, agar-agar, calcium carbonate, potato or tapioca starch, alginic acid, croscarmellose sodium, complex silicates, and sodium carbonate, (e) solution retarders, as for example paraffin, (f) absorption accelerators, as for example, quaternary ammonium compounds, (g) wetting agents, as for example, cetyl alcohol, and glycerol monostearate, magnesium stearate and the like (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid dosage forms as described above can be prepared with coatings and shells, such as enteric coatings and others well known in the art. They may contain pacifying agents, and can also be of such composition that they release the active compound or compounds in a certain part of the intestinal tract in a delayed manner. Examples of embedded compositions that can be used are polymeric substances and waxes. The active compounds can also be in microencapsulated form, if appropriate, with one or more of the above-mentioned excipients.

Liquid dosage forms for oral administration include pharmaceutically acceptable emulsions, solutions, suspensions, syrups, and elixirs. Such dosage forms are prepared, for example, by dissolving, dispersing, etc., a compound(s) of the invention, or a pharmaceutically acceptable salt thereof, and optional pharmaceutical adjuvants in a carrier, such as, for example, water, saline, aqueous dextrose, glycerol, ethanol and the like; solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide; oils, in particular, cottonseed oil, groundnut oil, corn germ oil, olive oil, castor oil and sesame oil, glycerol, tetrahydrofurfuryl alcohol, polyethyleneglycols and fatty acid esters of sorbitan; or mixtures of these substances, and the like, to thereby form a solution or suspension.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions for rectal administrations are, for example, suppositories that can be prepared by mixing the compounds of the present invention with for example suitable non-irritating excipients or carriers such as cocoa butter, polyethyleneglycol or a suppository wax, which are solid at ordinary temperatures but liquid at body temperature and therefore, melt while in a suitable body cavity and release the active component therein.

Dosage forms for topical administration of a compound of this invention include ointments, powders, sprays, and inhalants. The active component is admixed under sterile conditions with a physiologically acceptable carrier and any preservatives, buffers, or propellants as may be required. Ophthalmic formulations, eye ointments, powders, and solutions are also contemplated as being within the scope of this invention.

Generally, depending on the intended mode of administration, the pharmaceutically acceptable compositions will contain about 1% to about 99% by weight of a compound(s) of the invention, or a pharmaceutically acceptable salt thereof, and 99% to 1% by weight of a suitable pharmaceutical excipient. In one example, the composition will be between about 5% and about 75% by weight of a compound(s) of the invention, or a pharmaceutically acceptable salt thereof, with the rest being suitable pharmaceutical excipients.

Actual methods of preparing such dosage forms are known, or will be apparent, to those skilled in this art; for example, see Remington's Pharmaceutical Sciences, 18th Ed., (Mack Publishing Company, Easton, Pa., 1990). The composition to be administered will, in any event, contain a therapeutically effective amount of a compound of the invention, or a pharmaceutically acceptable salt thereof, for treatment of a disease-state in accordance with the teachings of this invention.

The compounds of the invention, or their pharmaceutically acceptable salts, are administered in a therapeutically effective amount which will vary depending upon a variety of factors including the activity of the specific compound employed, the metabolic stability and length of action of the compound, the age, body weight, general health, sex, diet, mode and time of administration, rate of excretion, drug combination, the severity of the particular disease-states, and the host undergoing therapy. The compounds of the present invention can be administered to a patient at dosage levels in the range of about 0.1 to about 1,000 mg per day. For a normal human adult having a body weight of about 70 kilograms, a dosage in the range of about 0.01 to about 100 mg per kilogram of body weight per day is an example. The specific dosage used, however, can vary. For example, the dosage can depend on a number of factors including the requirements of the patient, the severity of the condition being treated, and the pharmacological activity of the compound being used. The determination of optimum dosages for a particular patient is well known to those skilled in the art.

EXAMPLES

Exemplary in vitro and in vivo protocols can be found in Gendreau S B, Ventura R, Keast P, et al., *Inhibition of the T790M Gatekeeper Mutant of the Epidermal Growth Factor Receptor by EXEL-7647*, Clin Cancer Res 3713, 13(12) (2007), which is hereby incorporated in its entirety by reference.

Compound Preparation

For in vitro assays, a 10 mmol/L stock solution of XL-647 was prepared in DMSO and diluted in optimal assay buffers or culture medium. The final DMSO assay concentration did not exceed 0.3% (v/v). For in vivo studies, XL-647 was formulated for oral administration by dissolution of dry powder, either the HCl or tosylate salt, in sterile filtered (0.45 μm; Nalge Nunc International) saline (0.9% USP, Baxter Corp.) or in sterile water (Baxter). All compounds were mixed by vortexing and sonicated in a water bath to disrupt large particles. All dosing solutions/suspensions were prepared fresh daily.

Example 1

BPK Model of ARPKD

The effectiveness of XL-647 in treating ARPKD was tested using the BPK model of ARPKD. bpk mice have a BALB/c background, and contain the same mutation in the EGFR gene that is seen in murine and human ADPKD. These animals were housed in Medical College of Wisconsin vivarium facilities. All animal experiments were conducted in accordance with policies of the NIH Guide for the Care and Use of Laboratory Animals and the Institutional Animal Care and Use Committee of the Medical College of Wisconsin.

Beginning on post-natal day 7 (PN-7), entire litters from proven bpk heterozygous breeders include homozygous (diseased) as well as heterozygous and wild type animals were injected with XL-647 dosed every other day at 7.5 or 15 mg/kg or every day at 15 mg/kg. Animals were treated from PN-7 through PN-21 and evaluated for extent of disease. The identity of bpk+/+ animals can be readily determined post-mortem by the presence of greatly enlarged kidneys. On PN-21, the study was terminated and animals were sacrificed. The mass of each animal was determined. Both kidneys from each animal were excised and weighed. The kidney weight to body weight ratio (KW/BW) was determined by the following formula: KW/BW=[mass of both kidneys]/[mass of animal].

In addition, renal cystic index (CI) was calculated. Lectins specific to the proximal tubules (PTs) (lotus tetragonolobus [LTA]) and collecting tubules (CTs) (*Dolichos biflorus* agglutins [DBA]) were stained and used to assess severity of cystic dilations on a scale from 0-5. Renal function was assessed by obtaining BUN and creatinine levels via cardiac puncture. MUCA was measured after keeping the animals without water for 12 hrs.

The results shown in Table 1, demonstrate that XL-647 significantly reduced kidney weight in bpk mice treated 21.8% (7.5 mg/kg q.d.: 1.61±0.23) and 40.3% (15 mg/kg q.d.: 1.28±0.09). KW/BW decreased 21.5% (7.5 mg/kg q.d.: 15.34±1.26) and 36.7% (15 mg/kg q.d.) with treatment. Reduced kidney size also reflects a decreased CT-CI in treated bpk mice by 25% and 45.8% respectively in 7.5 mg and 15 mg/kg q.d.

Example 2

PCK Model

XL-647 was used in the PCK rat model, an orthologous model of ARPKD, to determine its effectiveness in inhibiting ErbB2. The phenotype of the PCK rat is different from that of humans in that it has a slower disease progression and slower decline in renal function. The PCK rats came from a mutated colony of Sprague-Dawley rats from Fujita Health University and were housed at the Medical College of Wisconsin. All animal experiments were conducted in accordance with policies of the NIH Guide for the Care and Use of Laboratory Animals and the Institutional Animal Care and Use Committee of the Medical College of Wisconsin.

From PN30 to PN 90, PCK (diseased) rats received XL-647 at 7.5 mg/kg/q.d. and 15 mg/kg/q.d. by gavage. Two hours after last injection on PN90 the rats were sacrificed and the kidneys and liver were removed and weighed. Post-mortem measurements included KW/BW ratio and

TABLE 1

Weight and Kidney Morphology in PRIM-001-Treated and Control BALB/C and bpk Mice on PN Day 21

| Parameter | BALB/C mice (N) | | | | bpk mice (N) | | | |
|---|---|---|---|---|---|---|---|---|
| | Sham (N = 8) | Vehicle (N = 8) | 7.5 mg/kg/day (N = 7) | 15 mg/kg/day (N = 7) | Sham (N = 8) | Vehicle (N = 14) | 7.5 mg/kg/day (N = 7) | 15 mg/kg/day (N = 10) |
| Body Weight (g) | 10.21 ± 0.23 | 10.83 ± 0.79 | 10.67 ± 0.93 | 10.06 ± 0.26 | 10.35 ± 0.52 | 10.52 ± 0.64 | 10.46 ± 1.16 | 9.96 ± 0.47 |
| Kidney Weight (g) | 0.15 ± 0.01 | 0.16 ± 0.01 | 0.14 ± 0.02 | 0.13 ± 0.01 | 2.04 ± 0.27 | 2.06 ± 0.30 | 1.61 ± 0.23 | 1.28 ± 0.09 |
| Kidney/Body weight (%) | 1.42 ± 0.06 | 1.45 ± 0.06 | 1.33 ± 0.07 | 1.25 ± 0.10 | 19.71 ± 2.00 | 19.53 ± 1.76 | 15.34 ± 1.26 | 12.36 ± 1.14 |
| CT-CI† | 0 | 0 | 0 | 0 | 4.60 ± 0.55 | 4.80 ± 0.45 | 3.60 ± 0.55 | 2.60 ± 0.55 | p-value for bpk vehicle treated vs XL647 treated bpk mice:
* $p < 0.05$;
** $p < 0.001$ The results in Table 2 show that treatment with XL-647 significantly improves renal function. BUN levels decreased 42.0% with 7.5 mg/kg q.d. and 60.5% with 15 mg/kg q.d. while creatinine levels decreased 8.3% and 25% respectively. Improvement in MUCA measurements in bpk mice treated with XL-647 was 20.1% and 66.2% respectively. Western blot analysis was used to confirm the effectiveness of XL-647.

cystic index (CI) using renal sections from the cortex, medulla, and papilla. CT-CI was then determined from cystic index which was based on renal cyst size at 15 day intervals from PN0 to PN135. Renal function was assessed with BUN and creatinine levels from cardiac puncture.

Table 3 shows that PCK rats treated with XL-647 showed a significant reduction in KW/BW ratio with a corresponding decrease in kidney weight by 13.4% (7.5 mg/kg q.d.:

TABLE 2

Assessment of Renal Function in PRIM-001-Treated and Control BALB/C and bpk Mice on PN Day 21

| Parameter | BALB/C mice (N) | | | | bpk mice (N) | | | |
|---|---|---|---|---|---|---|---|---|
| | sham | vehicle | 7.5 mg/kg/day | 15 mg/kg/day | sham | vehicle | 7.5 mg/kg/day | 15 mg/kg/day |
| BUN (mg/dL) | 21.13 ± 2.23 (8) | 19.38 ± 1.06 (8) | 19.00 ± 2.24 (7) | 19.29 ± 1.60 (7) | 104.4 ± 25.56 (8) | 109.3 ± 18.80 (14) | 63.43 ± 24.28 (7) | 43.20 ± 13.99 (10) |
| Creatinine (mg/dL) | 0.28 ± 0.10 (8) | 0.24 ± 0.05 (8) | 0.24 ± 0.05 (7) | 0.29 ± 0.07 (7) | 0.56 ± 0.12 (8) | 0.48 ± 0.11 (14) | 0.44 ± 0.10 (7) | 0.36 ± 0.10 (10) |
| MUCA (mOsmol) | 1080 ± 52.4 (6) | 1044 ± 35.8 (5) | 1029 ± 50.1 (4) | 1029 ± 28.7 (4) | 487.5 ± 105.1 (7) | 466.3 ± 93.8 (8) | 560.0 ± 71.3 (4) | 775.0 ± 100.5 (6) | p-value for diseased vehicle treated vs XL647 treated mice:
* $p < 0.05$;
** $p < 0.001$ 5.77±0.47) and 26.0% (15 mg/kg q.d.: 4.93±0.42). By reducing kidney size, there is a reduction in CT cysts. Table 3 shows that treatment with XL-647 decreases CT-CI by 19.6% and 35.7% for 7.5 mg and 15 mg/kg q.d. respectively.

TABLE 3

Weight and Kidney Morphology in Control SD Rats and Vehicle and PRIM-001-Treated PCK Rats on PN Day 90

| Parameter | SD rat (sham) (N = 12) | SD rat (vehicle) (N = 10) | PCK rat (sham) (N = 6) | PCK rat (vehicle) (N = 12) | PCK rat (7.5 mg/kg/day) (N = 8) | PCK rat (15 mg/kg/day) (N = 8) |
|---|---|---|---|---|---|---|
| Body Weight (g) | 355.9 ± 12.58 | 369.8 ± 19.46 | 394.2 ± 23.11 | 393.8 ± 21.01 | 384.5 ± 23.69 | 379.4 ± 15.39 |
| Kidney Weight (g) | 3.44 ± 0.45 | 3.58 ± 0.25 | 6.87 ± 0.26 | 6.66 ± 0.60 | 5.77 ± 0.47 | 4.93 ± 0.42 |
| Kidney/Body weight (%) | 0.96 ± 0.10 | 0.97 ± 0.04 | 1.74 ± 0.05 | 1.69 ± 0.08 | 1.5 ± 0.08 | 1.31 ± 0.08 |
| CT-CI | NA | NA | 7.17 ± 0.75 | 7.00 ± 0.60 | 5.63 ± 0.74 | 4.50 ± 0.92 |

\* p-value for vehicle treatment of SD rat vs PCK rat: $p < 0.001$;
\*\* p-value for vehicle treated vs PRIM-001 treated PCK rats: $p < 0.05$;
\*\*\* p-value for vehicle treated vs PRIM-001 treated PCK rats: $p < 0.001$ Table 4 displays measurements of renal function. PCK rats that received treatment had decreased BUN levels by 19.2% (7.5 mg/kg q.d.: 27.50±3.74) and 28.8% (15 mg/kg q.d.: 24.25±4.3). Western blot analysis was used to confirm and validate the effectiveness of XL-647.

TABLE 4

Clinical Kidney Chemistry Parameters in Control SD Rats and Vehicle and PRIM-001-Treated PCK Rats on PN Day 90

| Parameter | SD rat (sham) (N = 12) | SD rat (vehicle) (N = 10) | PCK rat (sham) (N = 5) | PCK rat (vehicle) (N = 12) | PCK rat (7.5 mg/kg/day) (N = 8) | PCK rat (15 mg/kg/day) (N = 8) |
|---|---|---|---|---|---|---|
| BUN (mg/dL) | 21.17 ± 1.19 (12) | 22.40 ± 1.55 (10) | 34.00 ± 4.74 (5) | 32.71 ± 4.57 (12) | 27.50 ± 3.74 (8) | 24.25 ± 4.30 (8) |
| Creatinine (mg/dL) | 0.33 ± 0.08 (12) | 0.34 ± 0.12 (10) | 0.54 ± 0.5 (5) | 0.54 ± 0.09 (12) | 0.48 ± 0.09 (8) | 0.46 ± 0.07 (8) | p-value for diseased vehicle treated vs XL647 treated mice:
\* $p < 0.05$;
\*\* $p < 0.001$ Example 3

In Vitro Biochemical Assay for XL-647 Inhibition

The effect of the XL-647 compound on the activity of several kinases, including EGFR, ErbB2/HER2, and KDR/VEGFR2, was measured using one of three assay formats. Dose-response experiments were done using 10 different inhibitor concentrations in 384-well microtiter plates. The ATP concentration used for each assay was equivalent to the $K_m$ for each kinase. $IC_{50}$ values were calculated by nonlinear regression analysis using the four-variable equation: $Y=\min+(\max-\min)/[1+/IC_{50}N]$, where Y is the observed signal, [I] is the inhibitor concentration, min is the background signal in the absence of enzyme (0% enzyme activity), max is the signal in the absence of inhibitor (100% enzyme activity), $IC_{50}$ is the inhibitor concentration required at 50% enzyme inhibition, and N represents the empirical Hill slope as a measure of cooperativity. Results are summarized in Table 5.

A radiometric $^{33}$P-Phosphoryl transfer kinase assay was used to measure EphB4, insulin-like growth factor-I receptor (IGFR-1), and insulin receptor (IRK) activity. Reactions were performed in 384-well white, clear bottom, high-binding microtiter plates (Greiner). Plates were coated with 2 μg/well peptide substrate in a 50 μL volume. The coating buffer contained 40 μg/mL EphB4 and IRK substrate poly(Ala-Glu-Lys-Tyr) or IGFR-1 substrate poly(Glu-Tyr) 6:2:5:1 (Perkin-Elmer), 22.5 mmol/L $Na_2CO_3$, 27.5 mmol/L $NaHCO_3$, 150 mmol/L NaCl, and 3 mmol/L $NaN_3$. The coated plates were washed once with 50 μL assay buffer following overnight incubation at room temperature. Test compound and either 5 nmol/L EphB4 (residues E605-E890 of human EphB4 containing a six histidine $NH_2$-terminal tag, expressed in a baculovirus expression system and purified using metal chelate chromatography), 4 nmol/L insulin-like growth factor-I receptor (residues M954-C1367 of human insulin-like growth factor-I receptor, Proqinase GmbH), or 15 nmol/L insulin receptor 1 (residues P948-S1343 of human insulin receptor 1, Proqinase) were combined with [$^{33}$P]g-ATP (5 μmol/L, 3.3 μCi/nmol) in a total volume of 20 μL. The reaction mixture was incubated at room temperature for 1.5 to 2.5 h and terminated by aspiration. The microtiter plates were subsequently washed six times with 0.05% Tween-PBS buffer. Scintillation fluid (50 μL/well) was added and incorporated $^{33}$P was measured by liquid scintillation spectrometry using a MicroBeta scintillation counter (Perkin-Elmer).

A Luciferase-coupled chemiluminescence assay was used to measure EGFR and KDR (VEGFR2) activity. Kinase activity was measured as the percentage of ATP consumed following the kinase reaction using luciferase-luciferincoupled chemiluminescence. Reactions were conducted in 384-well white, medium-binding microtiter plates (Greiner). Kinase reactions were initiated by combining XL-647, 3 µmol/L ATP, 1.6 µmol/L substrate (poly(Glu,Tyr) 4:1; Perkin-Elmer), and either EGFR (7 nmol/L, residues H672-A1210 of human EGFR, Proqinase) or KDR (5 nmol/L, residues D807-V1356 of human KDR, Proqinase) in a 20 mL volume. The reaction mixture was incubated at room temperature for 4 h. Following the kinase reaction, a 20 µL aliquot of Kinase Glo (Promega) was added and luminescence signal was measured using a Victor2 plate reader (Perkin-Elmer). Total ATP consumption was limited to 50%.

An AlphaScreen tyrosine kinase assay was used to measure ErbB2 and Flt-4 activity. Donor beads coated with streptavidin and acceptor beads coated with PY100 antiphosphotyrosine antibody (Perkin-Elmer) were used. Biotinylated poly(Glu,Tyr) 4:1 was used as the substrate. Substrate phosphorylation was measured by luminescence following donor-acceptor bead addition followed by complex formation. Test compound, 3 µmol/L ATP, 3 nmol/L biotinylated poly(Glu,Tyr) 4:1, and 1 nmol/L ErbB2 (residues Q679-V1255 of human ErbB2, Proqinase) or Flt-4 (residues D725-R1298 of human Flt-4, Proqinase) were combined in a volume of 20 µL Assay Buffer (20 mM TrisHCl, pH 7.5, 10 mM $MgCl_2$, 3 mM $MnCl_2$, 1 mM DTT, 0.01% Triton) in a 384-well white, medium-binding microtiter plate (Greiner). Reaction mixtures were incubated for 1 h at room temperature. Reactions were quenched by addition of 10 µL of 15 to 30 µg/mL AlphaScreen bead suspension containing 75 mmol/L HEPES (pH 7.4), 300 mmol/L NaCl, 120 mmol/L EDTA, 0.3% bovine serum albumin, and 0.03% Tween 20. After 2 to 16 h of incubation at room temperature, plates were read using an AlphaQuest reader (Perkin-Elmer).

TABLE 5

In vitro kinase inhibition profile of XL-647.

| Kinase | $IC_{50}$ ± SD (nmol/L) |
|---|---|
| EGFR | 0.3 ± 0.1 |
| ErbB2 | 16 ± 3 |
| KDR | 1.5 ± 0.2 |
| Flt-4 | 8.7 ± 0.6 |
| EphB4 | 1.4 ± 0.2 |
| Src | 10.3 ± 2.0 |
| IGF1R | >10,000 |
| InsR | >26,000 |

Results are presented as mean±SD of at least three independent determinations.

Mechanism of action studies for EGFR, ErbB2, KDR, and EphB4 confirmed that XL-647 is a reversible and ATP competitive inhibitor. High concentrations of enzyme and XL-647 (>>$K_i$) were combined and incubated for 2 hours on ice. The following concentrations of enzyme and XL-647 were used: 200 nM EphB4, 400 nM XL-647; 0.5 nM EGFR, 5 nM XL-647; 3 nM KDR, 1000 nM XL-647. Enzymatic activity was measured by standard methods after dilution of the enzyme-inhibitor complex. Activity was compared to a DMSO control treated under identical conditions.

TABLE 6

$K_i$ Determinations for XL-647 Against Selected Kinases.

| Parameters | EphB4 | EGFR | ErbB2 | KDR |
|---|---|---|---|---|
| Reversible | Yes | Yes | Yes | Yes |
| ATP-Competitive | Yes | Yes | Yes | Yes |
| $K_M$ (µM) (ATP) | 5.0 | 0.5 | 2.5 | 0.7 |
| $K_i$ (nM) | 1 | 0.05 | 3 | 0.6 |

Example 3

In Vitro Biochemical Screen for Specificity of XL-647

The specificity of XL-647 was assessed against a panel of pharmacological targets, including receptors, transporters, and enzymes (NovaScreen, Hanover, Md.). At a single in vitro concentration of 10 µM, XL-647 was shown to interact with very few of the pharmacological targets (Table 7). Only the human serotonin transporter was inhibited with an $IC_{50}$<1 µM ($IC_{50}$=188 nM). Effects were also observed at muscarinic receptors, α2-adrenergic receptor and dopamine transporter, which exhibited $IC_{50}$ values of 1-2.7 µM.

TABLE 7

NovaScreen Assay Panel Against XL-647

| Target Assay | Inhibition, 10 µM XL-647 | $IC_{50}$ (nM) |
|---|---|---|
| Adenosine, Non-selective | 47.89% | |
| Adrenergic, Alpha 1, Non-selective | 49.40% | |
| Adrenergic, Alpha 2, Non-selective | 84.56% | 1800 |
| Adrenergic, Beta, Non-selective | 18.01% | |
| Dopamine Transporter | 87.14% | 2480 |
| Dopamine, Non-selective | 34.88% | |
| GABA A, Agonist Site | 1.07% | |
| GABA-B* | −1.19% | |
| Glutamate, AMPA Site | 10.79% | |
| Glutamate, Kainate Site | 0.89% | |
| Glutamate, NMDA Agonist Site | −1.66% | |
| Glutamate, NMDA, Glycine (Stry-insens Site)* | 6.46% | |
| Glycine, Strychnine-sensitive | 12.95% | |
| Histamine, H1 | 59.82% | |
| Histamine, H2* | 45.68% | |
| Histamine, H3 | 38.64% | |
| Melatonin, Non-selective | 0.18% | |
| Muscarinic, M1 (Human Recombinant)* | 98.13% | 2330 |
| Muscarinic, M2 (Human Recombinant)* | 98.73% | 1180 |
| Muscarinic, Non-selective, Central | 97.91% | 2570 |
| Muscarinic, Non-selective, Peripheral | 87.74% | 2650 |
| Nicotinic (a-bungarotoxin insensitive) | 53.97% | |
| Norepinephrine Transporter | −5.38% | |
| Opiate, Non-selective | 39.73% | |
| Serotonin Transporter | 100.94% | 188 |
| Serotonin, Non-selective | 24.52% | |
| Sigma, Non-selective | 50.90% | |
| Estrogen | 15.75% | |
| Testosterone (cytosolic) | 18.09% | |
| Calcium Channel, Type L (Dihydropyridine Site) | 46.77% | |
| Calcium Channel, Type N | 16.82% | |
| Potassium Channel, ATP-Sensitive | 5.02% | |
| Potassium Channel, Ca2+ Act., VI | 17.02% | |
| Potassium Channel, Ca2+ Act., VS | 22.72% | |
| Sodium, Site 2 | 88.06% | |
| NOS (Neuronal-Binding) | 16.80% | |
| GABA A, BDZ, alpha 1, Central | 7.34% | |
| Leukotriene B4, LTB4 | 32.17% | |
| Leukotriene D4, LTD4 | −11.89% | |
| Thromboxane A2 (Human) | 1.51% | |
| Corticotropin Releasing Factor, Non-selective | 32.32% | |

TABLE 7-continued

NovaScreen Assay Panel Against XL-647

| Target Assay | Inhibition, 10 µM XL-647 | IC$_{50}$ (nM) |
|---|---|---|
| Oxytocin | −2.59% | |
| Platelet Activating Factor, PAF* | 11.72% | |
| Thyrotropin Releasing Hormone, TRH | 4.59% | |
| Angiotensin II, AT1 (Human) | 6.85% | |
| Angiotensin II, AT2 | 16.64% | |
| Bradykinin, BK2 | 48.81% | |
| Cholecystokinin, CCK1 (CCKA) | 47.54% | |
| Cholecystokinin, CCK2 (CCKB) | 17.12% | |
| Endothelin, ET-A (Human) | −11.07% | |
| Endothelin, ET-B (Human) | −13.61% | |
| Galanin, Non-Selective | 1.57% | |
| Neurokinin, NK1 | 20.44% | |
| Neurokinin, NK2 (NKA) (Human Recombinant)* | 34.23% | |
| Neurokinin, NK3 (NKB) | 19.96% | |
| Vasoactive Intestinal Peptide, Non-selective | 17.02% | |
| Vasopressin 1 | 32.83% | |
| Acetylcholinesterase | 49.40% | |
| Choline Acetyltransferase | 1.27% | |
| Glutamic Acid Decarboxylase | −8.46% | |
| Monoamine Oxidase A, Peripheral | 1.66% | |
| Monoamine Oxidase B, Peripheral | 2.03% | |

XL-647 was inactive against a panel of 10 tyrosine kinases (including the insulin and the insulin-like growth factor-1 receptor) and 55 serine-threonine kinases (including cyclin-dependent kinases, stress-activated protein kinases, and protein kinase C isoforms).

Further screening was performed using the biochemical assay methods of Example 2. Additional description of the components and concentrations are summarized in Table 8, Table 9, and Table 10, below. The results of screening are found in Table 11.

TABLE 8

Assay Components for Radiometric Kinase Assays

| Enzyme | [Enz] | [ATP] | Substrate | [subs] (µg/well) | T (min) | Assay Buffer | Construct |
|---|---|---|---|---|---|---|---|
| Flt-1 | 6 nM | 5 µM | poly-EY | 2 | 120 | 20 mM TrisHCl, pH 7.5, 10 mM MgCl$_2$, 3 mM MnCl$_2$, 1 mM DTT, 0.01% Triton | Human, cytoplasmic domain, N- GST-Factor X, ProQinase |
| Flt-1 | 6 nM | 5 µM | poly-EY | 2 | 120 | 20 mM TrisHCl, pH 7.5, 10 mM MgCl$_2$, 3 mM MnCl$_2$, 1 mM DTT, 0.01% Triton | Human, cytoplasmic domain, N- GST-Factor X, ProQinase |
| Tie-2(Tek) | 15 nM | 5 µM | poly-AEKY | 5 | 120 | 20 mM TrisHCl pH 7.5, 10 mM MgCl$_2$, 0.03% Triton, 1 mM DTT | Human, K956-S1390, N-GST-His6-Thrombin, ProQinase |
| PKC-epsilon | 600 pM | 2 uM | MBP | 1.2 | 90 | 20 mM Hepes, 10 mM MgCl$_2$, 1mM CaCl$_2$, 0.03% Triton X-100, 1 mM DTT | Human, PanVera |
| PKC-eta | 200 pM | 2 uM | MBP | 1 | 90 | 20 mM Hepes, 10 mM MgCl$_2$, 1 mM CaCl$_2$, 0.03% Triton X-100, 1 mM DTT | Human, PanVera |
| Chk1 | 10 nM | 10 µM | MBP | 2 | 120 | 1X STX Buffer (5 mM HEPES, pH 7.6, 15 mM NaCl, 0.01% BGG Bovine IgG), 10 mM MgCl$_2$, 1 mM DTT, 0.02% Triton | Human, N- GST-tag, Upstate Bio-technology |
| Chk2 | 20 nM | 30 µM | MBP | 2 | 120 | 1X STX Buffer, 10 mM MgCl$_2$, 1 mM DTT, 0.02% Triton | Human, 5-543, N-GST/C-His, Upstate Bio-technology |
| Plk-1 | 100 nM | 5 µM | Casein | 2.5 | 120 | 20 mM TrisHCl pH 8.0, 10 mM MgCl$_2$, 0.02% CHAPS | Human, His6 |
| Cdc2 | 10 nM | 5 µM | MBP | 2 | 120 | 25 mM Hepes pH 7.5, 100 mM NaCl, 10 mM MgCl$_2$, 3 mM MnCl$_2$, 1 mM DTT, 0.01% Triton | Human, M1-M297/h cyclin B M1-V433, N-GST-His6-Thrombin, ProQinase |

TABLE 9

Assay Components for AlphaScreen Kinase Assays

| Enzyme | [Enz] | [ATP] | Substrate | [subs] | T (min) | Assay Buffer | Construct |
|---|---|---|---|---|---|---|---|
| FGFR1 | 1 nM | 3 µM | poly-EY | 2 nM | 60 | 20 mM TrisHCl, pH 7.5, 10 mM MgCl$_2$, 3 mM MnCl$_2$, 1 mM DTT, 0.01% Triton | Human, cytoplasmic domain, N- GST-HIS6, ProQinase |

TABLE 9-continued

Assay Components for AlphaScreen Kinase Assays

| Enzyme | [Enz] | [ATP] | Substrate | [subs] | T (min) | Assay Buffer | Construct |
|---|---|---|---|---|---|---|---|
| c-Kit | 1 nM | 3 μM | poly-EY | 3 nM | 60 | 20 mM TrisHCl, pH 7.5, 10 mM $MgCl_2$, 3 mM $MnCl_2$, 1 mM DTT, 0.01% Triton | Human, T544-V976, N- GST, ProQinase |
| Fyn | 10 pM | 3 μM | poly-EY | 5 nM | 60 | 20 mM TrisHCl, pH 7.5, 10 mM $MgCl_2$, 2 mM $MnCl_2$, 1 mM DTT, 0.02% Triton | Human, N- His6, Upstate Bio-technology |

TABLE 10

Assay Components for Chemiluminescent Kinase Assays

| Enzyme | [Enz] | [ATP] | Substrate | [subs] | T (min) | Assay Buffer | Construct |
|---|---|---|---|---|---|---|---|
| EphA2 | 20 nM | 3 μM | poly-EY | 1.6 μM | 180 | 20 mM TrisHCl, pH 7.5, 10 mM $MgCl_2$, 3 mM $MnCl_2$, 0.01% Triton | Human, N598-R890, N- His6 |
| c-Met | 10 nM | 1 μM | poly-EY | 1 μM | 120 | 20 mM TrisHCl pH 7.5, 10 mM $MgCl_2$, 0.02% Triton X-100, 1 mM DTT, 2 mM $MnCl_2$ | Human, P948-S1343, N- GST-tag, ProQinase |
| Abl | 15 nM | 1 μM | poly-EY | 2 μM | 120 | 20 mM TrisHCl, pH 7.5, 10 mM $MgCl_2$, 3 mM $MnCl_2$, 1 mM DTT, 0.01% Triton | Human, P118-S553, N- GST, ProQinase |
| Lck | 12 nM | 1 μM | poly-AEKY | 4 μM | 120 | 20 mM TrisHCl, pH 7.5, 10 mM $MgCl_2$, 3 mM $MnCl_2$, 1 mM DTT, 0.03% Triton | Human, Q225-P510, N- GST/C-terminal EF |
| Src | 1.6 nM | 3 μM | poly-EY | 1.6 μM | 180 | 20 mM TrisHCl, pH 7.5, 10 mM $MgCl_2$, 3 mM $MnCl_2$, 1 mM DTT, 0.01% Triton | Human, N- His-tag, Upstate Bio-tech |
| ZAP70 | 4 nM | 1 μM | poly-EY | 0.8 μM | 120 | 20 mM TrisHCl, pH 7.5, 10 mM $MgCl_2$, 3 mM $MnCl_2$, 1 mM DTT, 0.01% Triton | Human, MBL |
| PKA | 10 nM | 5 uM | MBP | 5 μM | 120 | 20 mM Hepes, pH 7.4, 10 mM $MgCl_2$, 1 mM DTT, 0.03% Triton. | Bovine (Heart), Upstate Bio-technology |
| MAP4K3 | 10 nM | 5 μM | MBP | 5 μM | 120 | 20 mM Hepes, pH 7.4, 10 mM $MgCl_2$, 1 mM DTT, 0.03% Triton. | Kinase domain, N- His6 |
| EMK | 30 nM | 250 nM | Casein | 1 μM | 180 | 20 mM Hepes, 10 mM $MgCl_2$, 1 mM $CaCl_2$, 2 mM $MnCl_2$, 0.03% CHAPS, 1 mM DTT | Human, N- His6 |
| GSK-3β | 5 nM | 3 μM | Phospho-Glycogen Synthase peptide | 5 μM | 90 | 20 mM Hepes, pH 7.4, 10 mM $MgCl_2$, 1 mM DTT, 0.03% Triton | Human, N-His6/Glu-Glu epitope, Upstate Bio-technology |

TABLE 11

Further In vitro Inhibition profile of XL-647

| Kinase | $IC_{50}$ ± SD (nmol/L) |
|---|---|
| EphA2 | 6.8 ± 0.8 |
| Flt1 | 56.5 ± 15.5 |
| PDGFR-α | 64.4 ± 7.2 |
| PDGFR-β | 345.7 ± 37.0 |
| c-Kit | 132.2 ± 8.2 |
| c-Abl | 336.8 ± 3.6 |
| FGFR1 | 855.3 ± 96.3 |
| Tie-2 | 54.0 ± 13.4 |
| ZAP-70 | 7806.0 ± 655.3 |
| c-Met | 332.0 ± 50.7 |
| Fyn | 41.0 ± 8.1 |
| Lck | 31.0 ± 0.3 |
| Blk | 15 |
| Yes | 1.1 |
| Fes | 474 |
| Lyn | 2 |
| CSK | 402 |

Enzymes with $IC_{50}$ values in excess of 1 μM include: AMPK, c-Raf, CamKII, CamKIV, CDK1, CDK2, CDK3, CDK5, CDK6, CDK7, CK2, GSK3β, IKKα, IKKβ, JNK1α, JNK2α, JNK3α, MAPK1, MAPK2, PRAK MEK1, MKK4, MKK6, MKK7β, MAP4K3, MAP4K5, p70S6K, PAK2, Plk1, CK1PRAK2, ROCK II, Rsk1, Rsk2, Rsk3, SAPK3, SAPK4, Syk. Enzymes with $IC_{50}$ values in excess of 10 μM include: Chk1, Chk2, Clk1, Clk2, EMK, MAPKAP2, PKBα, PKBβ, PKCα, PKC-γ, PKC-ε, PKC-ζ, PKA, p70S6K, SGK.

Example 4

In Vivo Cell-Based Activity Assay

The inhibition of EGFR by XL-647 was confirmed in vivo, using A431 human epidermoid carcinoma (American Type Culture Collection), MDA-MB-231 human adenocarcinoma (Georgetown University), H1975 NSCLC adenocarcinoma (American Type Culture Collection), and Lx-1 squamous cell carcinoma (Department of Oncology Drug Discovery, Bristol-Myers Squibb) cells. A431 contains overexpressed wt human EGFR. H1975 contains both an activating mutation in EGFR (L858R) and a second site mutation (T790M) that confers resistance to gefitinib and erlotinib. Lx-1 cells do not express endogenous EGFR, and were used to express exogenous EGFR constructs. Other cell lines are summarized in Table 12.

A431 and MDA-MB-231 cell lines were maintained and propagated as monolayer cultures in DMEM (Mediatech) containing L-glutamine supplemented with 10% heat-inactivated fetal bovine serum (Hyclone), 100 units/mL penicillin G, 100 µg/mL streptomycin (1% penicillin/streptomycin, Mediatech), and 1% nonessential amino acids (Mediatech) at 37° C. in a humidified 5% $CO_2$ incubator. H1975, and Lx-1 cell lines were maintained in complete RPMI 1640 (30-2,001; American Type Culture Collection; containing L-glutamine supplemented with 10% heat-inactivated fetal bovine serum, 1% penicillin/streptomycin, and 1% nonessential amino acids) at 37° C. in a humidified 5% $CO_2$ incubator. Other cell lines were maintained and propagated by similar methods in standard media.

The effect of XL-647 on wt EGFR was measured in vivo by a cell-based EGFR autophosphorylation assay in A431 cells. A431 cells were seeded at $5 \times 10^4$ per well in 96-well microtiter plates (3904 Costar, VWR) and incubated in fully supplemented DMEM for 16 h after which growth medium was replaced with serum-free DMEM and the cells were incubated for an additional 24 h. Serial dilutions of XL-647 (in triplicate) in serum free medium were added to the quiescent cells and incubated for 1 h before stimulation with 100 ng/mL recombinant human EGF (R&D Systems) for 10 min. Negative control wells did not receive EGF. After treatment, cell monolayers were washed with cold PBS and immediately lysed with cold lysis buffer (50 mmol/L Tris-HCl (pH 8.0), 150 mmol/L NaCl, 10% glycerol, 1% NP40, 0.1% SDS, 0.5% sodium deoxycholate, 1 mmol/L EDTA, 50 mmol/L NaF, 1 mmol/L sodium pyrophosphate, 1 mmol/L sodium orthovanadate, 2 mmol/L phenylmethylsulfonyl fluoride, 10 µg/mL aprotinin, 5 µg/mL leupeptin, 5 µg/mL pepstatin). Lysates were centrifuged, transferred to 96-well streptavidin-coated plates (Pierce) containing biotin-conjugated, mouse monoclonal anti-human EGFR (2 µg/mL; Research Diagnostics), and incubated for 2 h. Plates were washed thrice with TBST (25 mmol/L Tris, 150 mmol/L NaCl (pH 7.2), 0.1% bovine serum albumin, and 0.05% Tween 20) and incubated with horseradish peroxidase-conjugated anti-phosphotyrosine antibody (1:10,000; Zymed Laboratories). Horseradish peroxidase activity was determined by reading the plates in a Victor2 plate reader following addition of the ELISA Femto substrate (Pierce). $IC_{50}$ values were determined based on total EGFR tyrosine phosphorylation with XL-647 treatment versus total EGFR tyrosine phosphorylation with growth factor treatment alone, normalized to receptor levels.

The effect of XL-647 on wt and mutated EGFR was measured in vivo, using transiently transfected Lx-1 cells. Lx-1 cells were used because they lack background EGFR activity. A clone corresponding to the longest EGFR isoform (Genbank accession no. NM_005228.3/NP_005219.2 #21-176, Upstate Biotechnology) was used as a template to produce two mutant EGFR genes (coding for L858R and L861Q) by site-directed mutagenesis. The WT and the two sequence-verified mutants were transferred to a COOH-terminal Flag-tagged retroviral cytomegalovirus promoter-driven mammalian expression vector. The two Tet-On expression vectors, EGFR WT (Tet-On) and EGFRvIII (Tet-On), which were COOH-terminally Flag tagged, were generously provided by Dr. Abhijit Guha (University of Toronto, Toronto, Ontario, Canada).

Transient transfections of Lx-1 cells were done using Lipofectamine 2000 (Invitrogen) according to the manufacturer's protocol. For transfections of the WT, L858R, and L861Q constructs, 1 µg plasmid DNA was used for each transfection (each well of a 12-well plate). For transfections of Tet-controlled EGFR WT and variant III constructs, 0.5 µg of either construct was combined with 0.5 µg of the pTet-On plasmid (BD Biosciences) for each transfection. Cells were harvested 24 h after transfection and replated in either 96-well plates ($4 \times 10^4$ cells per well) for compound treatments or 12-well plates ($2 \times 10^5$ cells) for immunoblot assays. Expression of the EGFRvIII transgene was induced 24 h after transfection by adding 1 µg/mL doxycycline to the medium. These cells were maintained in the presence of doxycycline for the remainder of the experiment. After a 12-h incubation, the cells were serum starved (in fetal bovine serum-free medium) and immediately treated with the indicated compounds in triplicate for 24 h followed by a 10-min treatment with recombinant human EGF (100 ng/mL). Whole-cell lysates were made by adding 125 µL radioimmunoprecipitation assay buffer (Boston Bioproducts) containing protease inhibitors (Protease Inhibitor Cocktail Tablets, Roche) in addition to 50 mmol/L NaF, 1 mmol/L sodium pyrophosphate, 1 mmol/L sodium orthovanadate, 2 mmol/L phenylmethylsulfonyl fluoride, 10 µg/mL aprotinin, and 5 µg/mL leupeptin in each well for either EGFR phosphorylation ELISA or immunoblot.

For the EGFR phosphorylation ELISA, Reacti-Bind streptavidin-coated plates (Pierce) were coated with 2 µg/mL biotin-conjugated anti-Flag antibody (Sigma). Whole-cell lysates (10 µg) were then added to the anti-Flag-coated wells in a final volume of 100 µL for 2 h at room temperature and then washed thrice with TBST. The anti-phosphotyrosine horseradish peroxidase-coupled secondary antibody (1:10,000; Zymed) was used to detect phosphorylated EGFR (pEGFR; 1 h at room temperature followed by three washes with TBST). Horseradish peroxidase activity was determined by reading the plates in a Victor2 plate reader following addition of the ELISA Femto substrate.

TABLE 12

Inhibition of WT and mutant EGFR phosphorylation by XL-647 in A431 and Lx-1 cells.

| EGFR | IC50 (nmol/L) |
|---|---|
| WT (A431) | 1 |
| WT (pCMV/Lx-1) | 12 |
| L858R (pCMV/Lx-1) | 5 |
| L861Q (pCMV/Lx-1) | 10 |
| WT (pTet-On/Lx-1) | 5 |
| Variant III (pTet-On/Lx-1) | 74 |

The EphB4 autophosphorylation ELISA utilized EphB4/Hep3B cells. Cells were seeded at $2 \times 10^4$ cells/well onto 96-well microtiter plates (Costar 3904), in MEME (Cellgro) containing 10% FBS (Heat-Inactivated, Hyclone), 1% penicillin-streptomycin (Cellgro) and 450 µg/ml G418 (Invitrogen). The cells were then incubated at 37° C., 5% $CO_2$ for 24 h. Growth media was replaced with serum-free MEME and cells were incubated for an additional 16 h. A serial dilution of XL-647 in fresh serum-free media was added to the quiesced cells and incubated for 1 h prior to a 30 min stimulation with a mixture of recombinant mouse Ephrin B2/Fc chimera protein (2 µg/ml, R&D Systems) and goat anti-human IgG/Fc (20 µg/ml, Pierce). Negative control wells were not treated with growth factor. Following treatment, media was removed, the cell monolayer washed with cold PBS and immediately lysed with cold lysis buffer (50 mM Tris-HCl, pH 8.0, 200 mM NaCl, 0.5% NP-40, 0.2% sodium deoxcholate, 1 mM EDTA, 50 mM NaF, 1 mM sodium pyrophosphate, 1 mM sodium orthovanadate, 2 mM phenylmethylsulfonyl fluoride, 10 µg/ml aprotinin, 5 µg/ml leupeptin and 5 µg/ml pepstatin A). Lysates were centrifuged and incubated in blocked (1% BSA) high-binding 96-well plates (Costar 3925) coated with anti-mouse EphB4 (2.5 µg/ml, R&D Systems). Plates were then incubated with HRP-conjugated anti-phosphotyrosine cocktail (1:10,000, Zymed Laboratories, Inc) followed by the addition of a luminol-based substrate solution. Plates were read using a Victor spectrophotometer (Wallac). $IC_{50}$ values were determined based on total EphB4 receptor tyrosine phosphorylation with XL-647 treatment versus total EphB4 receptor tyrosine phosphorylation with growth factor treatment alone.

The EphA2 autophosphorylation ELISA utilized PC-3 (ATCC) cells. Cells were seeded at $2.5 \times 10^4$ cells/well onto 96-well microtiter plates (Costar 3904), in DMEM (Cellgro) containing 10% FBS (Heat-Inactivated, Hyclone), 1% penicillin-streptomycin (Cellgro), and 1% NEAA solution (Cellgro). The cells were then incubated at 37° C., 5% $CO_2$ for 16 h. Growth media was replaced with serum-free DMEM and cells were incubated for an additional 24 hr. A serial dilution of XL-647 in fresh serum-free media was added to the quiescent cells and incubated for 1 h prior to a 20 min stimulation with a mixture of recombinant mouse Ephrin A1/Fc chimera protein (1 µg/ml, R&D Systems) and goat anti-human IgG/Fc (10 µg/ml, Pierce). Negative control wells were not treated with growth factor. After treatment, media was removed, the cell monolayer washed with cold PBS and immediately lysed with cold lysis buffer. Lysates were centrifuged and incubated into 96-well streptavidin-coated plates (Pierce) coated with biotin-conjugated, mouse anti-phosphotyrosine, PY20 (2 µg/ml, Calbiochem). Plates were incubated with rabbit polyclonal anti-EphA2, C-20 (1:500, Santa Cruz Biotechnology, Inc), followed by secondary antibody (HRP-conjugated, goat anti-rabbit IgG, 1:1000 from Cell Signaling) and the addition of a luminol-based substrate solution. Plates were read with a Victor spectrophotometer (Wallac). $IC_{50}$ values were determined based on total EphA2 receptor tyrosine phosphorylation with XL-647 treatment versus total EphA2 receptor tyrosine phosphorylation with growth factor treatment alone.

The c-Kit autophosphorylation ELISA utilized HeLa (ATCC) cells. Cells were seeded at $6 \times 10^5$ cells/well onto 100 mm dish. 24 hours later, HeLa cells were transfected with a mammalian expression plasmid containing a CMV promoter operably linked to the open reading frame of human c-kit with a Flag epitope tag on the C-terminus. 24 hours later, c-Kit transfected HeLa cells were trypsinized and re-seeded at $6 \times 10^3$ cells/well into 96-well microtiter plates (Costar 3904), in DMEM (Cellgro) containing 10% FBS (Heat-Inactivated, Hyclone), 1% penicillin-streptomycin (Cellgro), and 1% NEAA solution (Cellgro). The cells were then incubated at 37° C., 5% $CO_2$ for 24 hr. Serial dilutions of XL-647 in fresh serum-free medium were added to the cells and incubated for 1 hr prior to recombinant human SCF stimulation (100 ng/ml, R&D Systems) for 10 min. Negative control wells were left unstimulated. Following stimulation, media was removed, the cell monolayer washed with cold PBS and immediately lysed with cold lysis buffer. Lysates were incubated in 96-well streptavidin-coated plates (Pierce) coated with biotin-conjugated, goat anti-human c-Kit (1 µg/ml, R&D Systems). Plates were washed 3× with TBST and incubated either with HRP-conjugated anti-phosphotyrosine (1:10,000, Zymed Laboratories, Inc) or HRP-conjugated anti-Flag(M2) (1:2,000, Sigma). Plates were washed again as described above followed by the addition of a luminol-based substrate solution and read with a Victor spectrophotometer (Wallac). IC50 values were determined based on c-Kit tyrosine phosphorylation with XL-647 treatment versus c-Kit tyrosine phosphorylation with SCF treatment alone, after normalization.

The Flt-4 autophosphorylation ELISA utilized COS cells. Cells were seeded at 200,000 cells per well in 6-well plates in DMEM with 10% FBS and grown at 5% $CO_2$ and 37° C. After 24 h growth, cells were transfected with 1 µg/well Flt-4 cDNA, using 3 µl FuGENE-6 (Roche). Cells were treated 24 hours after transfection with XL-647 in fresh, serum free DMEM for 1 hour, then stimulated with 300 ng/ml VEGF-C for 10 min. The cell monolayer was washed twice with cold PBS and harvested by scraping into 150 µl ice-cold lysis buffer. Cell lysates were centrifuged at 13,000 g for 15 min, diluted 1:10 in ice-cold PBS, and transferred to clear Streptavidin plates (Pierce) coated with anti-human VEGF-C (Flt-4) biotinylated goat IgG (2 µg/well, R&D Biosciences). After washing, anti-Flag M2 mouse IgG-HRP (Sigma 1 to 10,000 dilution) or anti phospho-tyrosine rabbit IgG-HRP (Zymed, 61-5820, 1:10,000) was used to detect total Flt-4 and phosphorylated Flt-4. Samples were normalized and $IC_{50}$ values were determined by comparing Flt-4 tyrosine phosphorylation with XL-647 treatment versus Flt-4 tyrosine phosphorylation with VEGF-C treatment alone.

The ErbB2 autophosphorylation ELISA utilized BT474 (ATCC) cells. Cells were seeded at $3 \times 10^4$ cells/well into 96-well microtiter plates (Costar 3904), in 1:1(DMEM:F12K) (Cellgro) containing 10% FBS (Heat-Inactivated, Hyclone), 1% penicillin-streptomycin (Cellgro), 1% NEAA solution (Cellgro), and 2% L-Glutamine (Cellgro). The cells were then incubated at 37° C., 5% $CO_2$ for 40 hr. Cells were treated with a serial dilution of XL-647 in fresh serum-free media and incubated for 1 hr. Following treatment, media was removed, the cell monolayer was washed with cold PBS and immediately lysed with cold lysis buffer. Lysates were centrifuged and transferred into blocked (1% BSA) 96-well high-binding plates (Costar 3925) coated with rabbit polyclonal anti-ErbB2 (1.3 µg/ml, Cell Signaling Technology). Plates were then incubated with HRP-conjugated, anti-phosphotyrosine cocktail (1:10,000, Zymed Laboratories, Inc), followed by the addition of a luminol-based substrate solution. Plates were read with a Victor spectrophotometer (Wallac). $IC_{50}$ values were determined based on total ErbB2 tyrosine phosphorylation with compound treatment versus total ErbB2 tyrosine phosphorylation with no compound treatment.

TABLE 13

Inhibition of Autophosphorylation by XL-647.

| Tyrosine Kinase | CellularIC50(nM) |
|---|---|
| EGFR | 1 |
| EphB4 | 3 |
| KDR | 137 |
| c-Kit | 90 |
| Flt-4 | 90 |
| ErbB2 | 552 |
| EphA2 | 1100 |
| PDGFRβ | >1200 |

Example 5

Immunoblot Analysis

Lysates of H1975 cells treated with XL-647 were analyzed by immunoblot. For the H1975 immunoblot studies, $3 \times 10^5$ cells were plated in each well (12-well plate) and incubated for 16 h in complete RPMI 1640, rinsed with fetal bovine serum-free RPMI 1640, and incubated with serial dilutions of test compounds in fetal bovine serum-free medium for 2 h followed by stimulation with 100 ng/mL human recombinant EGF for 10 min. Whole-cell protein lysates were prepared as described above and centrifuged for 10 min at 13,000×g at 4° C. to remove any insoluble material. Total protein was determined using bicinchoninic acid reagent and an equal amount of protein was combined with LDS loading buffer (Invitrogen) according to the manufacturer's instructions. Proteins were separated by gel electrophoresis on 4% to 15% polyacrylamide gels, transferred to nitrocellulose membranes, and detected by immunoblotting. Antibody:antigen complexes were detected using chemiluminescence. The following antibodies from Cell Signaling Technology were used at a 1:1,000 dilution: anti-EGFR, anti-pEGFR$^{Tyr1068}$, anti-AKT, anti-pAKT$^{Ser473}$, anti-ERK, and anti-pERK$^{Thr202/Tyr204}$. The anti-β-actin primary antibody (Accurate Chemical and Scientific) was used at 1:10,000 and the horseradish peroxidase-coupled secondary antibodies were purchased from Jackson ImmunoResearch and used at 1:5,000.

Immunoblotting showed that XL-647 inhibits phosphorylation of EGFR at 30 and 10 μmol/L, and also inhibits the phosphorylation of AKT and ERK, which are downstream of EGFR phosphorylation. An example of an immunoblot can be found in Gendreau S B, Ventura R, Keast P, et al., *Inhibition of the T790M Gatekeeper Mutant of the Epidermal Growth Factor Receptor by EXEL-7647*, Clin Cancer Res 3713, 13(12) (2007), which is hereby incorporated by reference.

Example 6

A431 Xenograft Model

Female severe combined immunodeficient mice and female athymic nude mice (NCr), 5 to 8 weeks of age and weighing ~20 to 25 g, were purchased from The Jackson Laboratory and Taconic, respectively. The animals were housed at the Exelixis vivarium facilities according to guidelines outlined by the Exelixis Institutional Animal Care and Use Committee. During all studies, animals were provided food and water ad libitum and housed in a room conditioned at 70° F. to 75° F. and 60% relative humidity.

Before treatment, H1975, A431, or MDA-MB-231 cells were harvested from exponentially growing cultures, detached by brief trypsinization, washed twice in cold HBSS, resuspended in ice-cold HBSS, and implanted either s.c. (H1975, $3 \times 10^6$ cells per mouse) or i.d. (A431, $1 \times 10^6$ cells per mouse) into the dorsal hind flank or s.c. into the mammary fat pad (MDA-MB-231, $1 \times 10^6$ cells per mouse). Palpable tumors were measured by caliper twice weekly until the mean tumor weight was in the range of ~80 to 120 mg. Tumor weight was determined by measuring perpendicular diameters with a caliper and multiplying the measurements of diameters in two dimensions: tumor volume (mm$^3$)/2=length (mm)×width (mm$^2$)/2. Tumor weight (mg) was extrapolated from tumor volume (mm3) by assuming a conversion factor of 1. On the appropriate day after implantation, mice were grouped (10 mice per group) such that the group mean tumor weight was ~100±15 mg. The mean tumor weight of each animal in the respective control and treatment groups was determined twice weekly during the dosing periods. Tumor xenografts were established in female mice and allowed to reach approximately 100 mg prior to treatment. An example is described in Gendreau S B, Ventura R, Keast P, et al., *Inhibition of the T790M Gatekeeper Mutant of the Epidermal Growth Factor Receptor by EXEL-7647*, Clin Cancer Res 3713, 13(12) (2007), which is hereby incorporated by reference.

The response of tumors to treatment was determined by comparing the mean tumor weight of the treatment group with the appropriate control group. Percentage inhibition of tumor growth was determined with the following formula: Percentage inhibition=$100 \times [1-(X_f-X_o)/(Y_f-Y_o)]$, where $X_f$ and $Y_f$ are the mean tumor weights of the treatment and control groups, respectively, on day f, and $X_o$ and $Y_o$ are the mean tumor weights of treatment and control groups respectively, on day zero (staged tumor weights after grouping)

For determination of compound levels in plasma following oral administration of XL-647, whole blood was placed in heparinized Eppendorf tubes on ice and centrifuged at 20,000×g for 4 min. The plasma supernatant (50 μL) was added to 100 μL internal standard solution (250 ng/mL internal standard in acetonitrile), mixed by vortexing, and centrifuged. Sample extract (20 μL) was assayed for XL-647 by LC/MS/MS analysis. Plasma levels were calculated using an authentic standard curve. The limit of quantification was 0.004 μmol/L (2 ng/mL) for XL-647. Mean values and SD were calculated for each time point and dose concentration was assessed.

For immunohistochemical analysis of H1975, MDA-MB-231 and other xenografts, tumors were excised after euthanasia and fixed in zinc fixative (BD Biosciences) for 48 h before being processed into paraffin blocks. Serial sections at 5 μm were obtained from the area of largest possible surface for each tumor and stained using standard methods. The following antibodies were used: Ki67 (SP6; Labvision), CD31 (MECA.32; BD Biosciences), pERK$^{Thr202/Tyr204}$ (phospho-p44/42 mitogen-activated protein kinase; Cell Signaling Technology), pAKT$^{Ser473}$ (Cell Signaling Technology), and pEGFR$^{Tyr1068}$ (Cell Signaling Technology). For immunofluorescent staining, sections were then incubated with Alexa 594-conjugated goat anti-rabbit secondary antibody (Invitrogen) and mounted in Fluorescent Mounting Medium (DAKO) containing 4',6-diamidino-2-phenylindole (Molecular Probes) as a nuclear counterstain. Fluorescent staining was visualized using a Zeiss Axiolmager and digitally captured using a Zeiss high-resolution camera coupled to AxioVision image analysis software. Two to three non-overlapping representative fields were captured at ×200 or ×400 magnification depending on histologic readout and quantified using the integrated morphometric analysis functions in Metamorph software (Universal Imaging Corp.). Apoptotic cells were detected using terminal deoxynucleotidyl transferase-mediated dUTP nick end labeling in situ cell death detection kit according to the manufacturer's instructions (Roche Diagnostics GmbH).

CD31-positive tumor vessels, Ki67-positive proliferating cells, and pERK staining in each tumor section were identified and quantified using the integrated morphometric analysis functions in the ACIS automatic cellular imaging system (Clarient, Inc.) and reviewed by a blinded observer. Number of CD31-positive vessels were identified across 5 to 10 randomly chosen fields of equal size at ×100 magnification in viable tumor tissue and calculated as number of vessels per square millimeter for each tumor, averaged for each treatment group, and compared with vehicle-treated controls. Percentage Ki67-positive cells were calculated as the ratio between Ki67-positive cells divided by the total number of cells identified across 5 to 10 randomly chosen fields of equal size in viable tumor tissue. The results for each tumor and treatment group were averaged and compared with vehicle-treated controls. The level of pERK staining was determined as described above and calculated as the ratio of antibody staining divided by the total number of cells identified, averaged for each treatment group, and compared with vehicle-treated controls.

Results are presented as mean±SD or SE as indicated for each graph or table. For $IC_{50}$ comparison in the A431 cell viability experiment, two sample Student's t tests were applied to determine P values for each $IC_{50}$ pair assuming that the random fluctuations of replicates around the dose-response curve are distributed [log]normally with the individual replicates used as the 'sample size' for the t test (nine point dose response done in triplicate). For statistical analysis of immunohistochemical results from in vivo studies, two-tailed Student's t test analysis and Bonferroni correction were done to identify significant differences compared with vehicle control group (multiple use of a single vehicle control group) with a cumulative minimal requirement of $P<0.05$. Final tumor weight measurements at the end of the H1975 efficacy study and percentage pEGFR, pAKT, Ki67 index, CD31, and terminal deoxynucleotidyl transferase-mediated dUTP nick end labeling in H1975 xenografts were analyzed with one-way ANOVA followed by post hoc Student-Newman-Keul analysis for determination of statistical differences between XL-647 and erlotinib.

In A431 xenograft mice, once-daily oral administration of XL-647 (10, 30, and 100 mg/kg/day) for 14 days significantly inhibited tumor growth in a dose dependent manner. At 10 mg/kg/day, 65% tumor growth inhibition was seen, with evidence for cessation of tumor growth towards the end of the study. A dose of 100 mg/kg/day resulted in marked regression of tumors (starting weight: 109±20 mg; final weight: 36±15 mg).

Immunohistochemical analysis showed that treatment of subcutaneously grown A431 tumors in female athymic nude mice with XL-647 at 100 mg/kg qd×14 significantly increased the percentage of total tumor necrosis by 2.9-fold compared to vehicle-treated tumors (Table 14). The percentage of CD31-positive vessels in viable tumor tissue was significantly decreased by treatment with XL-647 at 10, 30, and 100 mg/kg. This inhibition of tumor angiogenesis demonstrated dose dependence. The percentage of Ki67-expressing cells in the A431 tumors was significantly reduced at all dose levels, indicating a reduction in the number of proliferating cells in the tumor at the end of the study.

TABLE 14

Summary of A431 Immunohistochemical Analyses for 14-Day Dosing

| Dose (mg/kg) | Necrosis % Increase | Necrosis Fold Increase | CD31 Analysis MVC | CD31 Analysis % Reduction | Ki67 Expression % of Cells | Ki67 Expression % Reduction |
|---|---|---|---|---|---|---|
| Vehicle | 21.2 ± 8.6 | NA | 27.9 ± 7.1 | NA | 37.6 ± 4.9 | NA |
| 10 | 20.7 ± 6.4 | 1.0 | 18.6 ± 9 | 33.5 | 17.6 ± 4.9 | 53.3 |
| 30 | 26.5 ± 18.6 | 1.3 | 15.9 ± 5.5 | 43.2 | 12.3 ± 5.5 | 67.2 |
| 100 | 61.7 ± 10.4 | 2.9 | 3.6 ± 2.9 | 87.3 | 6.5 ± 2 | 82.6 |

MVC, mean vessel count;
NA, not applicable.
Values are mean ± SD.

On Day 14 of dosing, whole blood was collected by terminal cardiac puncture and the plasma concentration profile of XL-647 determined by liquid chromatography with mass spectrometry (LC/MS/MS). XL-647 demonstrated a PK profile of extended plasma drug exposure with micromolar plasma concentrations observed up to 24 hours after administration of the last dose of the study at the 30 and 100 mg/kg doses.

Example 7

Additional Xenograft Oncology Models

Several additional models were used to explore the efficacy and potency of XL-647 with regard to tumor growth inhibition and tumor regression in vivo. The tumor cell lines used are representative of solid tumors and are listed in Table 15. The standard experimental design for these studies, as described in detail above, involved once-daily oral administration of XL-647 beginning when the established solid tumors reached a designated mass (approximately 100 mg for most xenograft models). Throughout the dosing period, tumor size was measured twice weekly (where applicable), and body weight was measured daily. XL-647 exhibited potent anti-tumor activity in these studies, with substantial regression observed for solid tumors. Tumors were excised at the termination of some studies and examined histologically for microvascular density (CD31 staining), proliferating cells (Ki67 staining), and necrosis (hematoxylin/eosin staining). Inhibition of tumor growth generally correlated well with increased tumor necrosis, decreased tumor vascularization, and decreased tumor cell proliferation index, suggesting that anti-angiogenic activity contributed to the potent anti-tumor efficacy of XL-647.

Tolerability was monitored in these studies by daily measurement of body weight. XL-647 appeared to be generally well-tolerated in mice without substantial body weight loss in dosing for 14 days at 100 mg/kg/day.

Of the lines examined, A431 and HN5 were the most sensitive, with efficacious XL-647 doses resulting in 50% tumor growth inhibition ($ED_{50}$) estimated at 5.9 mg/kg/day and 3.8 mg/kg/day following 14 or 28 days of dosing for the A431 model, respectively, and less than 3 mg/kg/day following 14 days of dosing for the HN5 model (summarized in Table 15).

TABLE 15

XL-647 ED$_{50}$ Values in Human Tumor Xenografts

| Human Tumor Xenograft[a] | Tissue of Origin | ED50 (mg/kg)[a] | |
|---|---|---|---|
| | | qd × 14 | qd × 28 |
| MDA-MB-231 | Breast | 21.9 | 22.9 |
| BT474 | Breast | 9.8 | 21.9 |
| HT-29 | Colon | 20.2 | 16.0 |
| A431 | Epidermis | 5.9 | 3.8 |
| Calu-6 | Lung | ND | 16.4 |
| PC-3 | Prostate | ND | 34.0 |
| H1975 | Lung | 17 | ND |
| HN5 | Head and Neck | <3 | ND |

A431, epidermoid carcinoma; BT474, breast carcinoma; Calu-6, NSCLC; H1975, NSCLC that contains both an activating mutation in EGFR (L858R) and a second site mutation (T790M) that confers resistance to gefitinib and erlotinib (Pao et al. 2005); HN5, head and neck carcinoma; HT-29, colon carcinoma; MDA-MD-231, breast carcinoma; ND, not done; PC-3, prostate carcinoma; qd, once daily.
[a]ED$_{50}$ = Dose required for 50% tumor inhibition. Tumor-bearing athymic mice were treated with XL647 for 14 or 28 days.

TABLE 16

Summary of H1975 Immunohistochemical Analyses for 14-Day Dosing.

| Dose (mg/kg) | TUNEL | | CD31 Analysis | | Ki67 Expression | |
|---|---|---|---|---|---|---|
| | % Cells | Fold increase | MVC | % Reduction | % Cells | % Reduction |
| Vehicle control | 1 ± 0.2 | NA | 62 ± 8 | NA | 35 ± 3 | NA |
| 10 | 6 ± 0.8 | 7.1[a] | 44 ± 10 | 30.0[b] | 27 ± 4 | 23.2[b] |
| 30 | 11 ± 1.4 | 11.9[a] | 34 ± 9 | 46.1[a] | 20 ± 5 | 41.9[a] |
| 100 | 15 ± 1.8 | 16.5[a] | 19 ± 11 | 69.6[a] | 8.9 ± 2 | 74.6[a] |

MVC, mean vessel count;
NA, not applicable.;
TUNEL, terminal deoxynucleotidyl transferase biotin-dUTP nick end labeling.
Values are mean ± SD.
[a]P < 0.0001.
[b]P < 0.005.

TABLE 17

Summary of H1957 Immunohistochemical Analyses of Phosphorylation for 14-Day Dosing.

| Dose (mg/kg) | Phospho-EGFR$^{Tyr1068}$ | | Phospho-ERK$^{Thr202/Tyr204}$ | | Phospho-AKT$^{Ser473}$ | |
|---|---|---|---|---|---|---|
| | % Cells | % Reduction | % Cells | % Reduction | % Cells | % Reduction |
| Vehicle control | 27 ± 1.8 | NA | 23 ± 2.6 | NA | 42 ± 2.0 | NA |
| 10 | 14 ± 1.9 | 49.0[a] | 20 ± 4.3 | 11.8 | 19 ± 2.1 | 53.6[a] |
| 30 | 12 ± 1.3 | 56.1[a] | 13 ± 4.9 | 41.8[a] | 12 ± 1.9 | 72.4[a] |
| 100 | 10 ± 1.8 | 63.7[a] | 10 ± 3.7 | 57.1[a] | 11 ± 1.9 | 74.4[a] |

NA, not applicable.
Values are mean ± SD.
[a]P < 0.0001.

The in vivo effect of XL-647 on the activity of target receptor tyrosine kinases (RTKs) (EGFR, HER2/ErbB2, VEGFR2/KDR) was assessed by measuring receptor phosphorylation levels in tumor xenografts (EGFR, HER2/ErbB2) or murine lung (VEGFR2/KDR) following oral (PO) administration of XL-647 (Table 18), using similar methods to those previously described.

TABLE 18

Summary of Inhibition of Phosphorylation by XL-647 in Lung and Xenograft Models

| | p-Y-EGFR | HER2/ErbB2 | | p-Y-VEGFR2/KDR |
|---|---|---|---|---|
| | | Phospho | Total | |
| Estimated IC$_{50}$ (plasma concentration) | 0.72 μM | 3.6 μM | <6.4 μM | 1.2 μM |
| Single Dose Duration of Action (100 mg/kg, >50% inhibition) | >72 h | >72 h | >96 h | ND |

IC$_{50}$, concentration required for 50% inhibition; ND, not determined; Phospho = phosphorylation level.
p-Y-EGFR, p-Y-HER2/ErbB2 (and total HER2/ErbB2 (and p-Y-VEGFR2/KDR analysis was performed in A431 and BT474 xenografts, and murine lung, respectively.

The data from these pharmacodynamic experiments show that, in vivo, XL-647 inhibits key RTKs involved in promotion of tumor proliferation and angiogenesis, and also involved in PKD (EGFR, HER2/ErbB2, VEGFR2/KDR). This provides support for the hypothesis that the efficacy of XL-647 against multiple xenografts results from inhibition of tumor cell division and host endothelial cell responses. In general there was a good correlation between increases in plasma drug concentrations and increased inhibition of receptor phosphorylation at the doses tested. Single doses of 100 mg/kg of XL-647 produced prolonged inhibition of receptor phosphorylation (>72 hours).

A comparison of the plasma exposure and pharmacodynamics for inhibition of EGFR showed dose dependency. A plasma concentration of 4 μM resulted in 89% inhibition of EGFR phosphorylation in A431 xenografts (Table 19). Based on the plasma concentration/phosphorylated EGFR inhibition relationship, 50% inhibition of EGFR phosphorylation is predicted to occur at a plasma concentration of 0.72 μM.

TABLE 19

Plasma Concentration of XL-647 Versus EGFR Inhibition

| Dose(mg/kg) | Mean (SD) Plasma Concentration (μM) | Inhibition of p-Y-EGFR |
|---|---|---|
| Vehicle | — | 0.0 |
| 3 | 0.42 (0.08) | 41.0 |
| 10 | 1.49 (0.35) | 70.0 |
| 30 | 4.01 (1.06) | 89.0 |
| 100 | 6.50 (1.39) | 93.0 |
| In Vivo IC50 | 0.72 | 50 |

EGFR, epidermal growth factor receptor; IC$_{50}$, concentration required for 50% inhibition; SD, standard deviation.
XL647 was administered 3.5 hours before EGF administration. p-Y-EGFR levels were measured 30 minutes after EGF administration The kinetics with which XL-647 affects tumor proliferation and vascularization were determined using quantitative immunohistochemistry and histology on sectioned MDA-MB-231 xenograft tumors taken from mice treated daily with XL-647 for 3, 5, or 7 days. Tumor proliferation was measured by staining for Ki67, which selectively identifies S-phase cells. The degree of tumor vascularization was measured by staining with the endothelial cell marker CD31 (Table 20).

TABLE 20

Effect of XL-647 On Proliferation and Vascularity
of MDA-MB-231 Tumor Cells In Vivo

| Dose (mg/kg) | Time (days) | Ki67 (% Reduction)[a] | CD31 (% Reduction)[a] |
|---|---|---|---|
| 100 | 3 | 9.62 | 76.5 |
|  | 5 | 33.8 | 90.18 |
|  | 7 | 48.7 | 95.7 |

[a]Relative to vehicle.

XL-647 at 100 mg/kg caused a rapid decrease in vascularity, with 76% inhibition evident by 3 days and almost complete loss of endothelial cells in the tumor by 7 days. A reduction in the number of proliferating cells occurred progressively for the duration of the experiment, with a 50% reduction seen by Day 7.

The rapid onset and extent of microvessel loss from these tumors strongly suggests that XL-647 impacts the survival of endothelial cells in the neovasculature, rather than inhibiting ongoing angiogenesis alone.

Example 8

Preclinical Examples

Nonclinical Pharmacokinetics

The nonclinical Pharmacokinetics (PK) of XL-647 was studied in mice, rats, dogs, and monkeys. Animals were dosed either once or daily over several days, as described in Table 21 and 22 below. A summary of results can also be found in Tables 21 and 22 below. XL-647 was dosed as a liquid formulation with 100% normal saline or as a solid in a gelatin capsule at 10 mg/kg or 30 mg/kg. Systemic drug exposure (i.e., AUC) appeared to increase approximately dose proportionally over lower dose ranges in rats (10-100 mg/kg), monkeys (2-20 mg/kg), and dogs (3-30 mg/kg), but less than dose proportionally over higher dose ranges in the single dose studies (200-2000 mg/kg in rats, 5-300 mg/kg in monkeys, and 100-1000 mg/kg in dogs). Minimal (<2-fold) accumulation of XL-647 in plasma was seen with repeated daily dosing. Mean $t_{max}$ values were approximately 4 to 8 hours, and plasma terminal half-lives ranged from 9.41 to 20.9 hours. No apparent gender-related differences in XL-647 PK were observed. Large volumes of distribution (i.e., >18 L/kg following IV administration) were seen in all species. XL-647 was orally bioavailable in mice, rats and dogs. The highest bioavailability was measured in dogs (63%-74%), and was similar for tablet and liquid formulations.

XL-647 showed moderately high protein binding, 91-96%, to plasma proteins in rat, mouse and human plasma as determined by ultrafiltration, using standard methods. Equilibrium dialysis indicated that XL-647 was 93-97.5% protein bound in human plasma.

TABLE 21

Nonclinical Single-Dose Pharmacokinetics of XL-647

| Study | Species | GLP | Route | Dose (mg/kg) | $AUC_{0-t}$ (ng · h/mL) | $C_{max}$ (ng/mL) | $t_{1/2}$ (hour) |
|---|---|---|---|---|---|---|---|
| XL-647-NC-011 | rat | yes | po | 200 | 29470 | 1001 | NA |
|  |  |  |  | 600 | 41241 | 1327 | NA |
|  |  |  |  | 2000 | 52961 | 1687 | NA |
| XL-647-NC-001 | dog | no | po | 100 | M: 8969 | 407 | 10.4 |
|  |  |  |  |  | F: 21174 | 1103 | 14.2 |
|  |  |  |  | 300 | M: 7793 | 936 | 12.7 |
|  |  |  |  |  | F: 17106 | 1608 | 12.1 |
|  |  |  |  | 1000 | M: 27251 | 3769 | 13.2 |
|  |  |  |  |  | F: 34211 | 5088 | 16.1 |
| XL-647-NC-012 | monkey | yes | po | 50 | M: 11119 | 485 | 20.5 |
|  |  |  |  |  | F: 11465 | 611 | 14.8 |
|  |  |  |  | 150 | M: 14532 | 737 | 19.8 |
|  |  |  |  |  | F: 7032 | 379 | 20.4 |
|  |  |  |  | 300 | M: 15116 | 547 | 20.7 |
|  |  |  |  |  | F: 13078 | 603 | 20.9 |

$AUC_{0-t}$, area under the plasma concentration-vs-time curve from 0 hours to last sampling timepoint;
$C_{max}$, maximum plasma concentration;
F, females;
GI, gastrointestinal;
GLP, Good Laboratory Practices;
HCT, hematocrit;
HGB, hemoglobin;
LOAEL, lowest observable adverse effect level;
M, males;
MTD, maximum tolerated dose;
NA, not available;
NOAEL, no observable adverse effect level;
po, orally;
RBC, red blood cell;
$t_{1/2}$, terminal half-life

TABLE 22

Nonclinical Repeat-Dose Pharmacokinetics of XL-647

| Study | Species | GLP | Route | Dose | $AUC_{0-24}$ (ng · h/mL) | $C_{max}$ (ng/mL) | $t_{1/2}$ (hour) |
|---|---|---|---|---|---|---|---|
| XL-647-NC-006 | monkey | no | oral | Phase 1, 50 mg/kg bid × 2, then terminated because of toxicity | M: 14508 F: 17449 | 755 912 | NC NC |
| | | | | Phase 1, 100 mg/kg qd × 2, then terminated because of toxicity | M: 19605 F: 27987 | 1220 2161 | 20.7 11.6 |
| | | | | Phase 1, 300 mg/kg qd × 2, then terminated because of toxicity | M: 38377 F: 21076 | 2941 1505 | 12.1 14.8 |
| | | | | Phase 2, 10 mg/kg qd × 7 | M: 3627c F: 4269 | 230c 216 | 14.7c 14.9 |
| XL-647-NC-013 | rat | yes | oral | 10 mg/kg qd × 14 | 2,013 | 138 | 11.4 |
| | | | | 30 mg/kg qd × 14 | 5,741 | 319 | 20.4 |
| | | | | 100 mg/kg qd × 12 | 18,311 | 909 | NC |
| XL-647-NC-014 | monkey | yes | oral | 2 mg/kg qd × 14 | M: 488 F: 450 | 28.4 38 | NA NA |
| | | | | 6 mg/kg qd × 14 | M: 1855 F: 1690 | 106 116 | NA NA |
| | | | | 20 mg/kg qd × 7 or 8b, then terminated because of toxicity observed on Days 6 and 7 | M: 3901 F: 3912 | 194 202 | NA NA |
| XL-647-NC-019 | rat | yes | oral | 1 mg/kg qd × 90 | 198 | 12.7 | 14.4 |
| | | | | 3 mg/kg qd × 90 | 776 | 50.4 | 20.4 |
| | | | | 10 mg/kg qd × 90 | 3433 | 183 | 16.4 |
| XL-647-NC-022 | rat | yes | oral | 3 mg/kg qd × 180 | NA | NA | NA |
| | | yes | | 10 mg/kg qd × 180 | NA | NA | NA |
| | | | | 30 mg/kg qd × 180 | NA | NA | NA |
| XL-647-NC-021 | monkey | NA | NG | 0.3 mg/kg qd × 180 | NA | NA | NA |
| | | | | 1 mg/kg qd × 180 | NA | NA | NA |
| | | | | 3 mg/kg qd × 180 | NA | NA | NA |
| | | | | 6 mg/kg qd × 270 | NA | NA | NA |

A/G ratio, albumin to globulin ratio;
ALT, alanine aminotransferase;
AST, aspartate aminotransferase;
AUC0-24, area under the plasma drug concentration time curve from 0 to 24 hours;
BUN, blood urea nitrogen;
Cmax, maximum plasma concentration;
F, females;
GI, gastrointestinal;
GLP, Good Laboratory Practices;
HGB, hemoglobin;
HCT, hematocrit;
M, males;
NA, not available;
NG, nasogastric;
NOAEL, no observable adverse effect level;
po , orally;
qd, daily;
t½, terminal half-life
a Determined after the last dose, reported as a mean, and, unless otherwise indicated, applicable to males and females combined
b Toxicokinetic values are for Day 7
cValues based 0-48 hr sampling on Day 7.

Example 9

Summary of Human Clinical Studies

XL-647 was supplied as 50-mg white to off-white tablets. These tablets are provided in two configurations: 1) white to off-white oval-shaped tablets, one side bisected and the other side plain, containing 50 mg of XL-647 in a 33.33% drug concentration formulation, and 2) white to off-white round tablets containing 50 mg of XL-647 in a 50% drug concentration formulation.

The composition for both immediate release, lactose-based formulations are provided in Table 23 and Table 24, below. Comparative dissolution studies of the two XL-647 formulations were evaluated under conditions relevant to in vivo bioavailability and have confirmed the comparability of both formulations. All study medication was stored at room temperature and inventoried according to applicable state and federal regulations. If study drug was re-packaged, it was dispensed in high-density polyethylene (HDPE) vials.

TABLE 23

Quantitative Unit Composition of the XL-647 Tablets (33.3% Formulation)

| Ingredient | % w/w | mg per Tablet |
|---|---|---|
| XL-647 Drug Substance | 33.33 | 50.00 |
| Lactose Monohydrate 80, NF | 40.00 | 60.00 |
| Microcrystalline Cellulose, NF (Avicel PH101) | 11.37 | 17.05 |

TABLE 23-continued

Quantitative Unit Composition of the
XL-647 Tablets (33.3% Formulation)

| Ingredient | % w/w | mg per Tablet |
|---|---|---|
| Hypromellose 2910 (HPMC), USP | 5.00 | 7.50 |
| Crospovidone, NF | 5.00 | 7.50 |
| Sodium Lauryl Sulfate, NF | 4.00 | 6.00 |
| Colloidal Silicon Dioxide (Cab-O-Sil M5P) | 0.70 | 1.05 |
| Magnesium Stearate, NF (Vegetable Grade) | 0.60 | 0.90 |
| Purified Water, USP | Removed during manufacturing | Removed during manufacturing |
| Total | 100.00 | 150.00 |

TABLE 24

Quantitative Unit Composition of the
XL-647 Tablets (50% Formulation)

| Ingredient | % w/w | mg/tablet |
|---|---|---|
| XL-647 Drug Substance | 50.00 | 50.00 |
| Lactose Monohydrate 80, NF | 25.70 | 25.70 |
| Microcrystalline Cellulose, NF (Avicel PH101) | 10.00 | 10.00 |
| Hypromellose 2910 (HPMC), USP | 3.00 | 3.00 |
| Crospovidone, NF | 7.00 | 7.00 |
| Sodium Lauryl Sulfate, NF | 3.00 | 3.00 |
| Colloidal Silicon Dioxide (Cab-O-Sil M5P) | 0.70 | 0.70 |
| Magnesium Stearate, NF (Vegetable Grade) | 0.60 | 0.60 |
| Purified Water, USP | Removed during manufacturing | Removed during manufacturing |
| Total | 100.00 | 100.00 |

NF, National Formulary; USP, United States Pharmacopeia.

Individual Studies were Performed as Follows:

Study XL-647-001: Subjects with advanced solid tumors (n=41) were dosed on a 14-day cycle intermittent dosing schedule (the "intermittent 5&9 schedule"). On day 1-5 subjects received XL-647, followed by 9 days (day 6-14) of no treatment. XL-647 was administered in the Intermittent 5&9 schedule at dose levels ranging from 0.06 to 7.00 mg/kg to 41 subjects with a variety of solid tumors. Enrollment is complete, and all subjects have been off study as of 31 May 2007. Subjects initially received a powder in bottle (PIB) formulation using mass-based dosing. The MTD was determined to be 4.68 mg/kg, which was converted to a fixed dose of 350 mg. The final cohort received a fixed dose of 350 mg in a tablet formulation.

Study XL-647-002: Subjects with advanced solid tumors were enrolled in successive cohorts to receive XL-647 in a single oral dose daily. A total of 31 subjects have been treated across 5 dose levels ranging from 75 to 350 mg. The MTD was determined to be 300 mg, and 18 subjects have been treated at this dose level.

Study XL-647-004: Healthy volunteers (n=24) were given a single 300-mg dose of XL-647 either in a fed or fasted state, then crossed over to the opposite arm 22 days later. Food effect on bioavailability was analyzed.

Study XL-647-005: Healthy volunteers (n=8) were given a single oral dose of 300 mg labeled XL-647 ($^{14}$C-XL-647), and drug metabolism and elimination was assessed. Absorption, metabolism, excretion, and mass balance were analyzed.

Study XL-647-201: Subjects with non-small-cell lung cancer (NSCLC) (n=52) of adenomacarcinoma histology, Stage IIIB, with malignant pleural effusion, or Stage IV previously untreated for metastatic disease were enrolled. Subjects were selected for clinical characteristics predictive of response to EGFR inhibitors (Asian, female, and/or minimal and remote smoking history). XL-647 was administered as either 350 mg on the Intermittent 5&9 schedule (n=41) or 300 mg on the daily schedule (n=13).

Study XL-647-203: Subjects (n=41) with relapsed or recurrent NSCLC (Stage IIIB or IV) with documented progressive disease after benefit from single agent treatment with erlotinib or gefitinib or with a known EGFR T790M mutation were enrolled. Subjects received XL-647 at 300 mg orally once daily.

As of 1 Aug. 2008, clinical safety data are available for 159 subjects with cancer treated with XL-647. The most common adverse events (AEs) experienced by subjects receiving single agent XL-647 (frequency ≥10%, in decreasing order of frequency) were diarrhea, rash, fatigue, nausea, dry skin, cough, dyspnoea, anorexia, electrocardiogram QT prolongation (machine-read), vomiting, constipation, dysgeusia, upper respiratory tract infection, abdominal pain, back pain, pyrexia, dizziness, and dry mouth. The majority of these AEs were Grade 1 or Grade 2 and did not result in study drug discontinuation. There have been no deaths attributed to study drug.

Anti-tumor activity has been observed in subjects receiving XL-647 in both the Intermittent 5&9 and daily administration schedule. In the Phase 1 studies using the intermittent schedule, one subject with NSCLC had stable disease until Day 228, when an unconfirmed partial response (PR) was obtained and 14 other subjects (including three subjects with NSCLC) had prolonged stable disease (SD) lasting greater than 3 months. In the second Phase 1 study, XL-647-002, 16 subjects, including 3 subjects with NSCLC, had achieved SD lasting greater than 3 months. Of the 38 evaluable subjects enrolled in Phase 2 Study XL-647-201 (front-line, in subjects selected for clinical characteristics to enrich for EGFR mutations) on the Intermittent 5&9 schedule, 10 had a PR and 17 subjects experienced SD lasting 3 months or more for a clinical benefit rate (PR+SD) of 71%. Of these subjects who achieved clinical benefit, six subjects whose tumor contained EGFR exon 19 deletions and one subject with an L858R mutation experienced PRs, and 2 with L858R point mutations had SD. In the second Phase 2 study in subjects with relapsed or recurrent NSCLC (Stage IIIB or IV, n=41) with documented progressive disease after benefit from single agent erlotinib or gefitinib or with a known EGFR T790M mutation, one subject achieved a PR, and 19 subjects achieved SD as their best response.

In a preliminary analysis of clinical pharmacokinetics (PK) data for subjects receiving oral doses of XL-647 on the Intermittent 5&9 schedule, area under the concentration time curve (AUC) and maximum plasma drug concentration (Cmax) generally increased in proportion with dose over the full dose range studied (ie, total doses of 3.4 to 586 mg). The median terminal half-life after 5 consecutive doses was approximately 60 hours, and appeared generally independent of dose. XL-647 was rapidly absorbed following oral administration, with a median $t_{max}$ of about 4 hours. Following daily oral dosing at 300 mg/day (MTD), XL-647 accumulated approximately 4-fold in plasma, with steady state achieved by about Day 15. The once-daily administration of 300 mg XL-647 resulted in an approximately 2-fold increase in average exposure over a 28-day period versus Intermittent 5 & 9 dosing with 350 mg.

Nonclinical and in vitro metabolic profiling studies suggest that XL-647 is a substrate for CYP3A4-mediated metabolism in human liver microsomes. XL-647 was an inhibitor of isozymes CYP2D6 and CYP2C8 in vitro but not CYP3A4 in human liver microsomes. XL-647 is orally bioavailable in multiple species and is highly protein bound (93-99%) in human plasma.

In a clinical food effects study (XL-647-004) in healthy subjects, AUC was increased approximately 18% in the presence of food, whereas $C_{max}$ only increased by about 5%. Therefore, the administration of XL-647 with food or when combined with drugs or substances that inhibit the activity of CYP3A4 may result in elevated XL-647 exposure.

Preliminary data from a mass balance study suggested that XL-647 was significantly metabolized and excreted primarily in the feces.

The invention claimed is:

1. A method of treating polycystic kidney disease (PKD) in a mammal, the method comprising administering a therapeutically effective amount of a compound of formula or a pharmaceutically acceptable salt thereof, to a mammal having PKD,
wherein the administering of the compound or pharmaceutically acceptable salt thereof is by way of a tablet or liquid dosage form.

2. The method of claim 1 wherein the dosage form is a tablet.

3. The method of claim 2 wherein the compound or pharmaceutically acceptable salt thereof is 50 wt % of the tablet.

4. The method of claim 2 wherein the tablet comprises 50 mg of the compound or pharmaceutically acceptable salt thereof.

5. The method of claim 4 wherein the compound or pharmaceutically acceptable salt thereof is 50 wt % of the tablet.

6. The method of claim 2 wherein the mammal is a human.

7. The method of claim 2 wherein the mammal is a feline.

8. The method of claim 7 wherein the feline is a Persian cat.

9. The method of claim 2 wherein the mammal is a human.

10. The method of claim 2 wherein the mammal is a feline.

11. The method of claim 10 wherein the feline is a Persian cat.

12. The method of claim 4 wherein the mammal is a human.

13. The method of claim 5 wherein the mammal is a human.

14. The method of claim 2 wherein the tablet comprises the following components and amounts:

| Component | Amount (% w/w) |
| --- | --- |
| the compound or pharmaceutically acceptable salt thereof | 50.00 |
| Lactose Monohydrate | 25.70 |
| Microcrystalline Cellulose | 10.00 |
| Hypromellose | 3.00 |
| Crospovidone | 7.00 |
| Sodium Lauryl Sulfate | 3.00 |
| Colloidal Silicon Dioxide | 0.70 |
| Magnesium Stearate | 0.60. |

15. The method of claim 14 wherein the tablet comprises 50 mg of the compound or pharmaceutically acceptable salt thereof and the mammal is a human.

16. The method according to claim 2 wherein the administration is once daily.

17. The method according to claim 7 wherein the administration is once daily.

18. The method according to claim 12 wherein the administration is once daily.

19. The method according to claim 13 wherein the administration is once daily.

20. The method according to claim 14 wherein the administration is once daily.

21. The method according to claim 15 wherein the administration is once daily.

22. The method according to claim 1 wherein the dosage form is a liquid.

23. The method according to claim 22 wherein the liquid dosage form is a water-based solution.

24. The method according to claim 23 wherein the formulation is administered in an amount of 0.3 to 6 mg of the compound to kg of the mammal.

25. The method of claim 24 wherein the mammal is a human.

26. The method of claim 24 wherein the mammal is a feline.

27. The method of claim 25 wherein the feline is a Persian cat.

* * * * *